United States Patent
Ozcan et al.

(10) Patent No.: US 9,588,037 B2
(45) Date of Patent: Mar. 7, 2017

(54) HIGH THROUGHPUT LENS-FREE THREE-DIMENSIONAL TRACKING OF SPERM

(71) Applicant: THE REGENTS OF THE UNIVERSITY OF CALIFORNIA, Oakland, CA (US)

(72) Inventors: Aydogan Ozcan, Los Angeles, CA (US); Ting-Wei Su, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 14/412,984

(22) PCT Filed: Jul. 12, 2013

(86) PCT No.: PCT/US2013/050334
§ 371 (c)(1),
(2) Date: Jan. 5, 2015

(87) PCT Pub. No.: WO2014/012031
PCT Pub. Date: Jan. 16, 2014

(65) Prior Publication Data
US 2015/0204773 A1    Jul. 23, 2015

Related U.S. Application Data

(60) Provisional application No. 61/671,619, filed on Jul. 13, 2012.

(51) Int. Cl.
*G01N 15/14*   (2006.01)
*G06T 7/20*    (2006.01)
(Continued)

(52) U.S. Cl.
CPC ......... *G01N 15/1463* (2013.01); *G01B 11/00* (2013.01); *G01B 11/24* (2013.01);
(Continued)

(58) Field of Classification Search
None
See application file for complete search history.

(56) References Cited

U.S. PATENT DOCUMENTS

| 4,896,967 A | 1/1990 | Douglas-Hamilton et al. |
| 5,895,749 A | 4/1999 | Alvarez |

(Continued)

FOREIGN PATENT DOCUMENTS

WO    WO 2012094523 A2    7/2012

OTHER PUBLICATIONS

Adjacent, Merriam-Webster, https://web.archive.org/web/20100410190247/http://www.merriam-webster.com/dictionary/adjacent, Accessed on Apr. 11, 2016.*

(Continued)

*Primary Examiner* — Jason Heidemann
*Assistant Examiner* — Brian Shin
(74) *Attorney, Agent, or Firm* — Vista IP Law Group LLP

(57) ABSTRACT

A system for three dimensional imaging of motile objects includes an image sensor and a sample holder disposed adjacent to the image sensor. A first illumination source is provided and has a first wavelength and positioned relative to the sample holder at a first location to illuminate the sample. A second illumination source is also provided having a second wavelength, different from the first wavelength, and positioned relative to the sample holder at a second location, different from the first location, to illuminate the sample. The first and second illumination sources are configured to simultaneously, or alternatively, sequentially illuminate the sample contained within the sample holder. Three (Continued)

dimensional positions of the motile objects in each frame are obtained based on digitally reconstructed projection images of the mobile objects obtained from the first and second illumination sources. This positional data is connected for each frame to obtain 3D trajectories of motile objects.

24 Claims, 13 Drawing Sheets

(51) Int. Cl.
- G06T 19/20 (2011.01)
- G01B 11/24 (2006.01)
- G01B 11/00 (2006.01)
- G01N 15/10 (2006.01)

(52) U.S. Cl.
CPC ............ *G06T 7/2086* (2013.01); *G06T 19/20* (2013.01); *G01N 2015/1006* (2013.01); *G01N 2015/1075* (2013.01); *G06T 2200/04* (2013.01); *G06T 2207/30004* (2013.01)

(56) References Cited

U.S. PATENT DOCUMENTS

| | | | |
|---|---|---|---|
| 5,935,800 A | 8/1999 | Alvarez | |
| 6,069,655 A * | 5/2000 | Seeley | H04N 7/181 348/154 |
| 6,327,032 B1 * | 12/2001 | Lajeunesse | F42B 35/00 356/390 |
| 6,357,285 B1 | 3/2002 | Allen | |
| 7,241,988 B2 | 7/2007 | Gruber et al. | |
| 7,427,991 B2 * | 9/2008 | Bruderlin | G06T 13/40 345/419 |
| 2004/0264855 A1 * | 12/2004 | Chen | G02B 6/4206 385/33 |
| 2006/0263829 A1 | 11/2006 | Evans et al. | |
| 2009/0032449 A1 | 2/2009 | Mueth et al. | |
| 2009/0179596 A1 * | 7/2009 | Willaert | H05B 37/0272 315/313 |
| 2009/0244530 A1 * | 10/2009 | Iida | G01N 21/95607 356/237.5 |
| 2010/0167336 A1 | 7/2010 | Son et al. | |
| 2012/0046203 A1 * | 2/2012 | Walsh | A61B 5/157 506/39 |
| 2012/0148141 A1 * | 6/2012 | Ozcan | G06K 9/0014 382/133 |
| 2013/0280752 A1 * | 10/2013 | Ozcan | G01N 21/4795 435/29 |
| 2013/0335599 A1 * | 12/2013 | Zhang | H04N 5/225 348/239 |

OTHER PUBLICATIONS

PCT International Preliminary Report on Patentability (Chapter I of the Patent Cooperation Treaty) for PCT/US2013/050334, Applicant: The Regents of the University of California, Form PCT/IB/326 and 373, dated Jan. 22, 2015 (8pages).
Segerink, L. I. et al., On-chip determination of spermatozoa concentration using electrical impedance measurements, Lab Chip 2010, 10, 1018-1024.
Seo, S. et al, Lensfree holographic imaging for on-chip cytometry and diagnostics, Lab Chip 2009, 9, 777-787.
Su, T. et al., Multi-angle lensless digital holography for depth resolved imaging on a chip, Opt. Express 2010, 18, 9690-9711.
Su et al., Compact and Light-Weight Automated Serren Analysis Platform Using Lensfree on-Chip Microscopy, Anal Chem. Oct. 1, 2010; 82(19): 8307-8312.
Hardie et al., Joint Map Registration and High-Resolution Image Estimation Using a Sequence of Undersampled Images, IEEE, vol. 6 No. 12, Dec. 1997.
Ozcan et al., Ultra wide-filed lens-free monitoring of cells on-chip, Lab on Chip 8, 89-106, Nov. 1, 2007.
Ozcan et al., Lens-free On-Chip Cytometry for wireless Health Diagnosis, IEEE LEOS Newsletter, Oct. 2008.
Seo et al., Lensfree On-chip Cytometry Using Tunable Monochromatic Illumination and Digital Noise Reduction, Multi-color LUCAS, Sep. 2008.
Su et al., Towards Wireless Health: Lensless On-Chip Cytometry, Biophotonics, Dec. 2008.
Su et al., High-Throughput Lensfree Imaging and Characterization of Heterogeneous Cell Solution on a Chip, Biotechnology and Bioengineering, Sep. 8, 2008.
Isikman et al., Lensfree Cell Holography on a Chip: From Holographic Cell Signatures to Microscopic Reconstruction, LEOS Annual Meeting Conf. Proceedings, Oct. 2009.
Mudanyali et al., Lensless On-chip Imaging of Cells Provides a New Tool for High-throughput Cell-Biology and Medical Diagistics, Journal of Visualized Experiments, Dec. 14, 2009.
Bishara et al., Lensfree on-chip microscopy over a wide field-of-view using pixel super-resolution, Optics Express, vol. 18 No. 11, May 24, 2010.
Coskun et al., Wide field-of-view lens-free fluorescent imaging on a chip, Lab Chip, 10(7), 824-827, Apr. 7, 2010.
Coskun et al., Lensless wide-field fluorescent imaging on a chip using compressive decoding of sparse objects, Optics Express, vol. 18 No. 10, May 5, 2010.
Khademhosseinieh et al., Lensfree color imaging on a nanostructured chip using compressive decoding, Applied Physics Letters, 97, 211112-1, Nov. 24, 2010.
Khademhosseinieh et al., Lensfree on-chip imaging using nanostructured surfaces, Applied Physics Letters, 96, 171106, Apr. 30, 2010.
Mudanyali et al., Compact, light-weight and cost-effective microscope based on lensless incoherent holography for telemedicine applications, Lab Chip, 10, 1417-1428, Apr. 19, 2010.
Ozcan, Smart technology for global access to healthcare, SPIE, Mar. 16, 2010.
Ozcan et al., Lensfree on-chip holography facilitates novel microscopy applications, SPIE, May 19, 2010.
PCT International Search Report for PCT/US2013/050334, Applicant: The Regents of the University of California, Form PCT/ISA/210 and 220, dated Oct. 17, 2013 (7pages).
PCT Written Opinion of the International Search Authority for PCT/US2013/050334, Applicant: The Regents of the University of California, Form PCT/ISA/237, dated Oct. 17, 2013 (6pages).
Isikman et al., Lens-free optical tomographic microscope with a large imaging volume on a chip, PNAS, May 3, 2011, vol. 108, No. 18, 7296-7301.
Crocker et al., Methods of Digital Video Microscopy for Colloidal Studies, Journal of Colloid and Interface Science, 179, 298-310 (1996).
Memmolo et al., On the holographic 3D tracking of in vitro cells characterized by a highly-morphological change, Opt. Express, 20, 28485-28493 (2012).

* cited by examiner

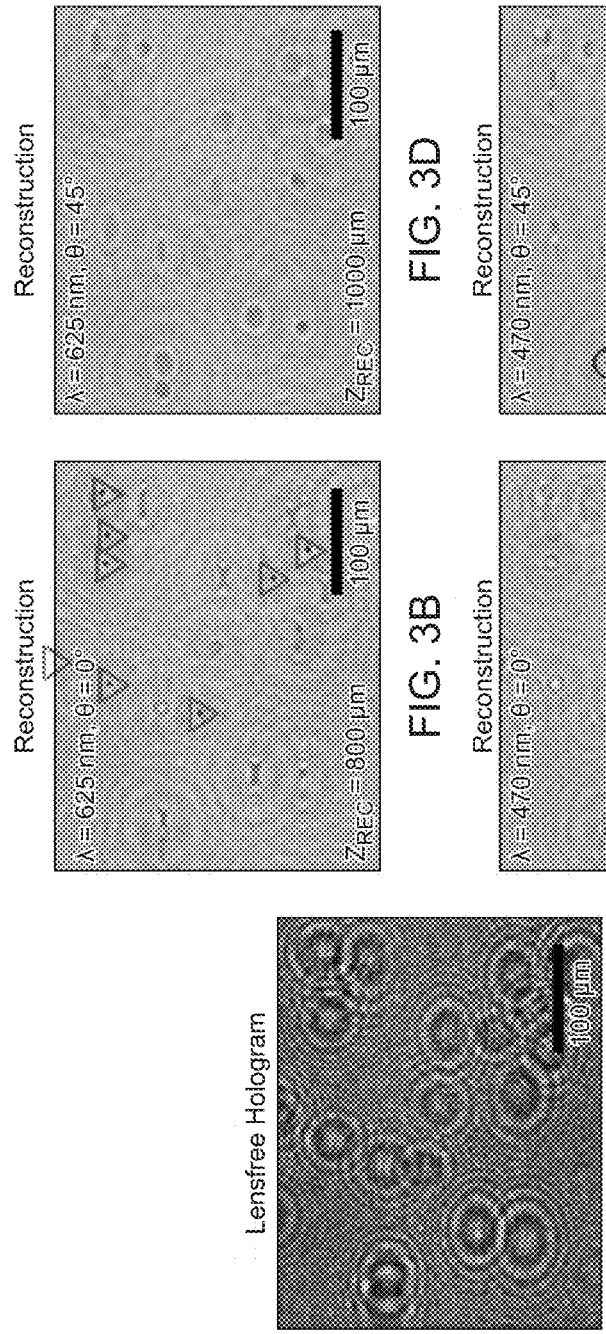

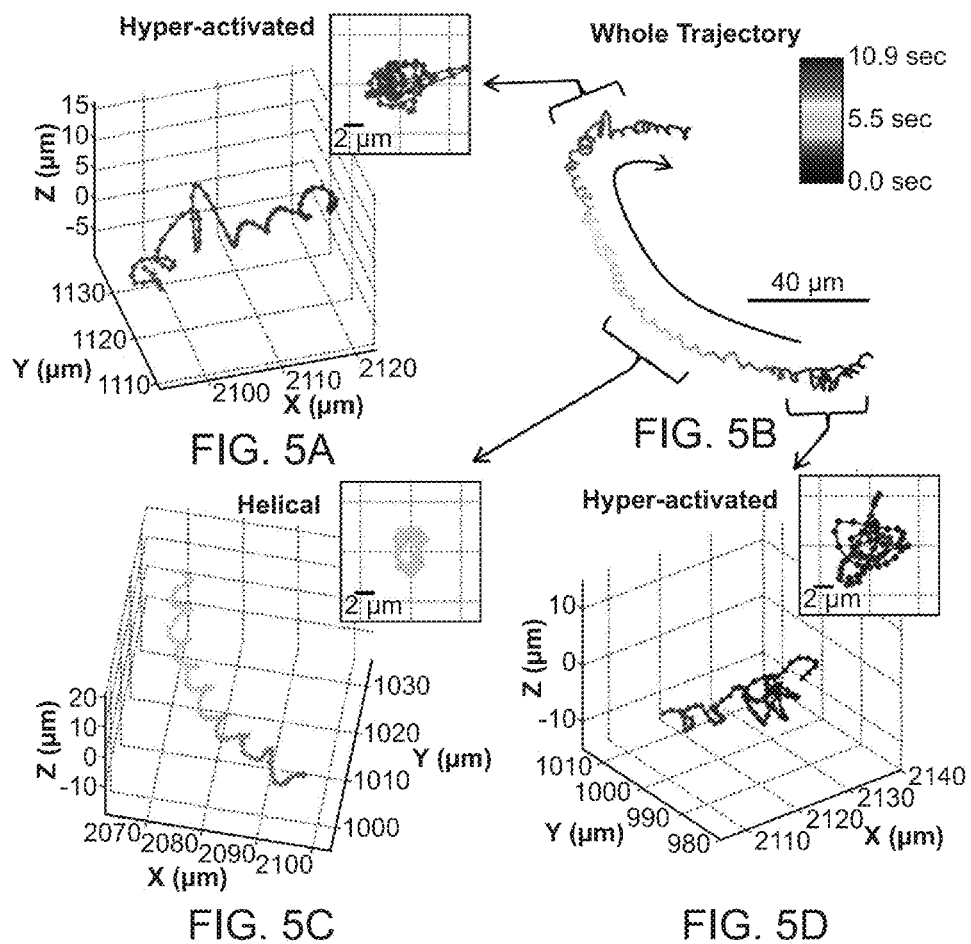

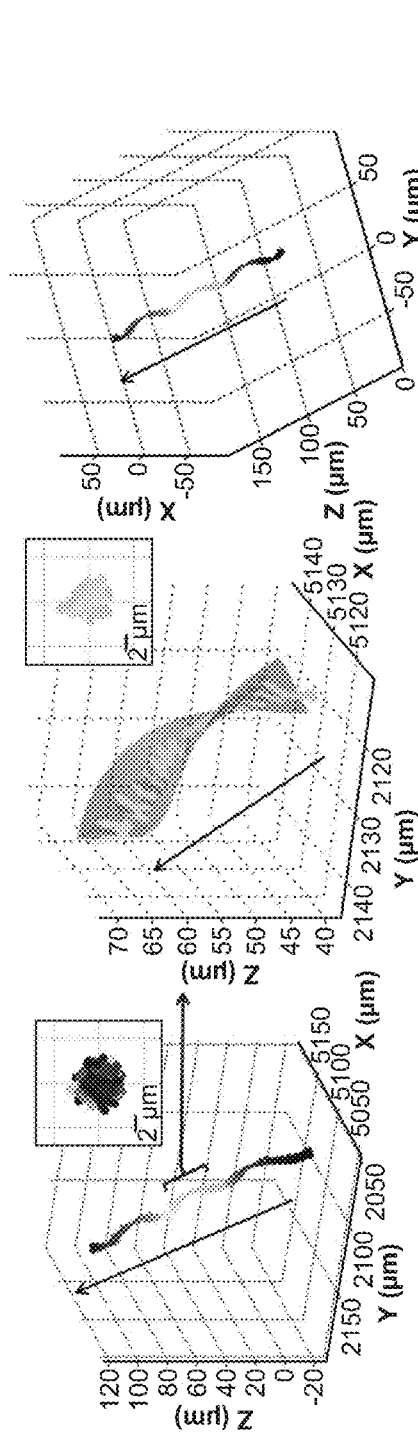
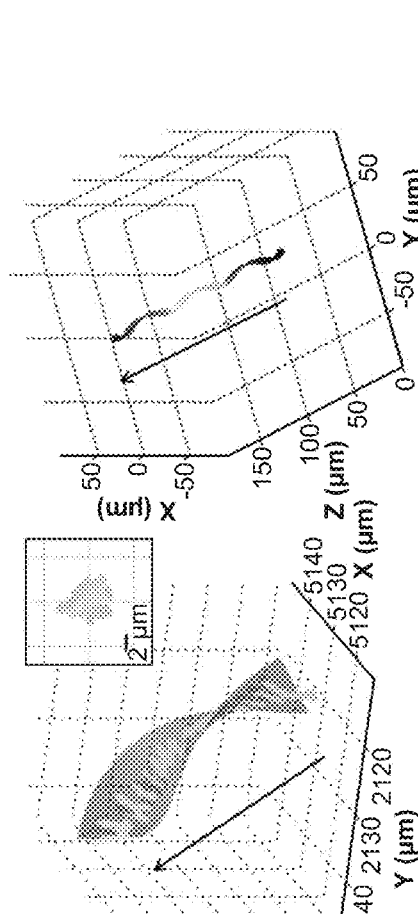
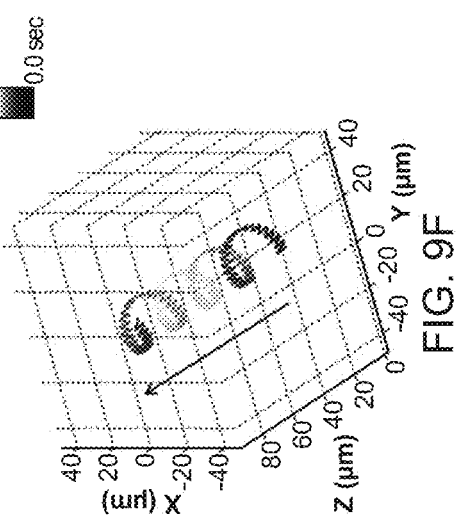
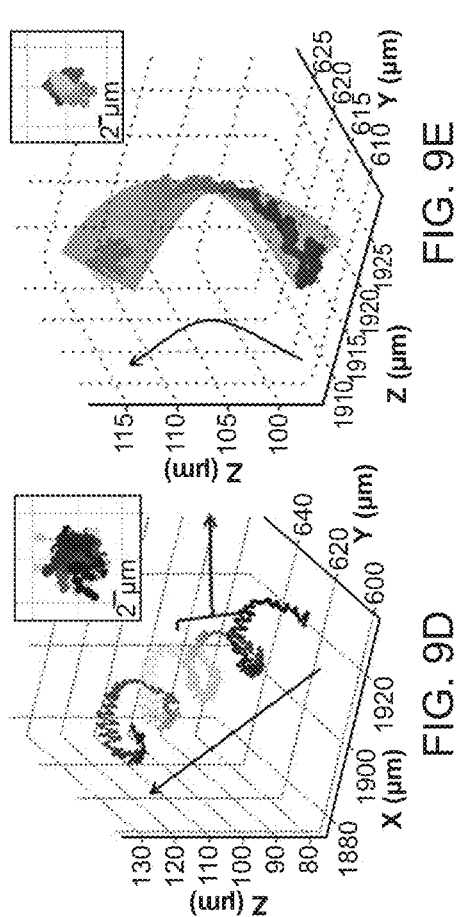
FIG. 9A  FIG. 9B  FIG. 9C
FIG. 9D  FIG. 9E  FIG. 9F

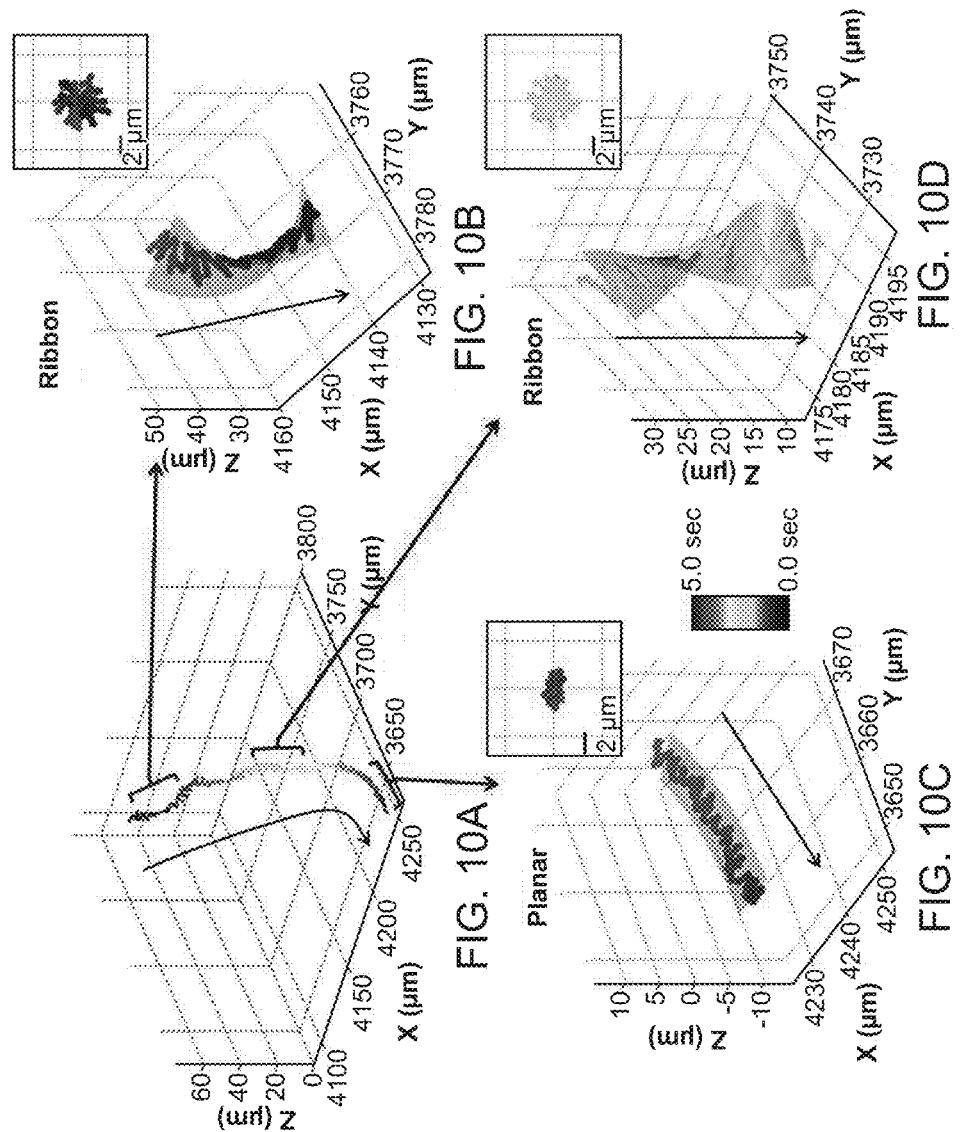

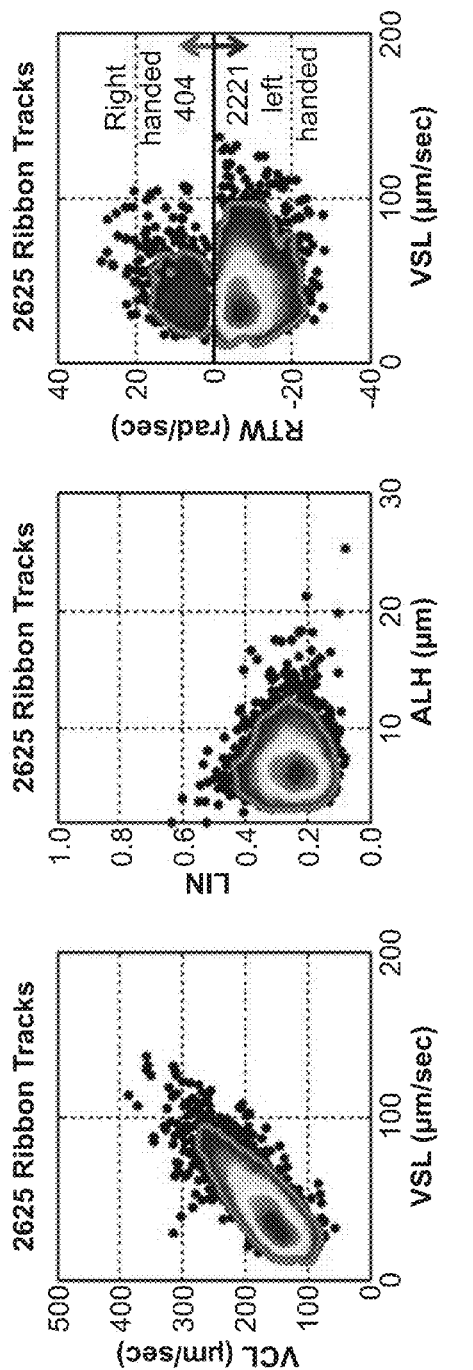

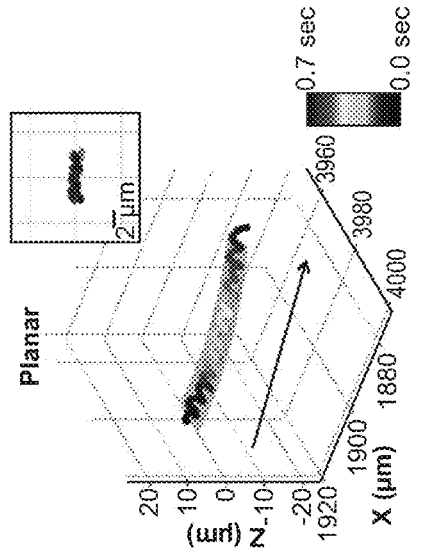
FIG. 12A Irregular
FIG. 12B Linear
FIG. 12C Planar
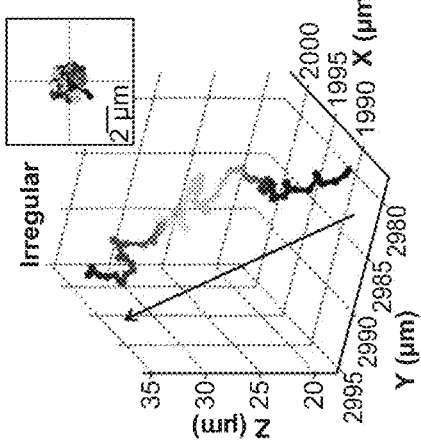
FIG. 12D Helical
FIG. 12E Ribbon
FIG. 12F Hyperactivated (Hyper-progressive)

HIGH THROUGHPUT LENS-FREE THREE-DIMENSIONAL TRACKING OF SPERM

RELATED APPLICATIONS

This Application is a U.S. National Stage filing under 35 U.S.C. §371 of PCT Patent Application No. PCT/US2013/050334, filed Jul. 12, 2013, which claims priority to U.S. Provisional Patent Application No. 61/671,619, filed on Jul. 13, 2012. The contents of the aforementioned applications are incorporated by reference herein. Priority is expressly claimed in accordance with 35 U.S.C. §§119, 120, 365 and 371 and any other applicable statutes.

FIELD OF THE INVENTION

The field of the invention generally relates to methods and devices for imaging of motile objects within a fluid solution. More particularly, the field of the invention pertains to systems and methods for the three-dimensional imaging and tracking of spermatozoa in a fluid solution.

BACKGROUND

Locomotion in an aqueous environment plays an important function in the lives of many micro-organisms, such as bacteria, protozoa, and sperm. Without this kind of self-propelled swimming act, these micro-organisms cannot actively find food, escape predators, or consummate fertilization. Understanding the swimming patterns of these types of motile micro-organisms and the underlying biophysical processes is important to advance existing knowledge in microbiology and has a number of practical applications. For example, it is known that highly motile sperm are generally associated with a higher fertility potential. Highly motile sperm are thought to have a higher quality of sperm which is one factor in successful pregnancies. Tests that are able to discern the quality of sperm are useful in addressing male infertility.

Identifying and quantifying of sperm swimming patterns also has applications for artificial insemination. Artificial insemination has become an indispensable tool in breeding industry of livestock animals, such as cattle, horse, swine and sheep. Currently, most dairy cattle and swine in developed countries are being reproduced through this technique. Although artificial insemination is currently not as widely practiced in the breeding of horses, an increasing number of horse breeders are adapting this new reproduction method as an economical way to enhance the desired traits of their horse breeds. An important factor for successful artificial insemination is to use high-quality semen specimens, especially the specimens containing sperm with high motility. However, most of the evaluations for horse sperm motility have been made using traditional lens-based optical elements. These systems and methods typically have shallow sample holders (~20 µm deep) to match the restricted depth-of-field of conventional optical microscope objective lenses. Such spatial confinement not only limits the observation of sperms to their two-dimensional (2D) dynamics but also modifies their native three-dimensional (3D) movement.

SUMMARY

In one embodiment, a system for three dimensional imaging of motile objects contained within a sample includes an image sensor and a sample holder configured to hold the sample, the sample holder disposed adjacent to the image sensor. The system further includes a first illumination source having a first wavelength and positioned relative to the sample holder at a first location to illuminate the sample and a second illumination source having a second wavelength, different from the first wavelength, and positioned relative to the sample holder at a second location, different from the first location, to illuminate the sample. The first illumination source and the second illumination source are configured to simultaneously illuminate the sample contained within the sample holder.

In another embodiment, a method for three dimensional tracking of motile objects contained within a sample is provided. The method includes simultaneously illuminating a sample holder containing the motile objects with a first illumination source and a second illumination source wherein the first illumination source and the second illumination source are located at different positions from one another and emit light at different wavelengths. A plurality of image frames over time are obtained of the motile objects with an image sensor disposed adjacent to the sample holder while the sample holder is illuminated. A projection image of the motile objects in each frame is digitally reconstructed based on illumination originating from the first illumination source. A projection image of the motile objects in each frame is digitally reconstructed based on illumination originating from the second illumination source. The x, y, and z positions of the motile objects in each frame is identified based on the digitally reconstructed projection images of the mobile objects obtained from the first and second illumination sources. The x, y, and z positions of the motile objects over a plurality of frames are then connected to form a three-dimensional track of the motile objects within the sample.

In still another embodiment, a method for three dimensional tracking of motile objects contained within a sample is provided. The method includes sequentially illuminating a sample holder containing the motile objects with a first illumination source and a second illumination source wherein the first illumination source and the second illumination source are located at different positions from one another and emit light at different wavelengths. A plurality of image frames over time are obtained of the motile objects with an image sensor disposed adjacent to the sample holder while the sample holder is illuminated. A projection image of the motile objects is digitally reconstructed in each frame based on illumination originating from the first illumination source. A projection image of the motile objects is digitally reconstructed in each frame based on illumination originating from the second illumination source. The x, y, and z positions of the motile objects are identified in each frame based on the digitally reconstructed projection images of the mobile objects obtained from the first and second illumination sources. The x, y, and z positions of the motile objects are then connected over a plurality of frames to form a three-dimensional track of the motile objects within the sample.

BRIEF DESCRIPTION OF THE DRAWINGS

FIG. 3A illustrates a lens-free image showing several sperm holograms recorded with a red LED at the vertical angle and a blue LED at the oblique angle simultaneously illuminating the sample.

FIG. 3B illustrates a digitally reconstructed image of the same region of interest shown in FIG. 3A with the conditions specified in the legend. The triangles in FIG. 3B mark the successful detection of the vertical projections of the sperms FIG. 3C illustrates a digitally reconstructed image of the same region of interest shown in FIG. 3A with the conditions specified in the legend. Reconstruction with parameters that are not matched to the original illumination conditions create weak noise at the background as illustrated in FIG. 3C.

FIG. 3D illustrates a digitally reconstructed image of the same region of interest shown in FIG. 3A with the conditions specified in the legend. Reconstruction with parameters that are not matched to the original illumination conditions create weak noise at the background as illustrated in FIG. 3D.

FIG. 3E illustrates a digitally reconstructed image of the same region of interest shown in FIG. 3A with the conditions specified in the legend. The circles in FIG. 3E mark the successful detection of the oblique projections.

FIG. 5A illustrates a ~1 second digitally extracted segment of the whole sperm trajectory of FIG. 5B. The inset image represents the front-view of the "straightened" trajectory of the sperm. This motion is hyper-activated.

FIG. 5B illustrates a 10.9 second long trajectory of human sperm.

FIG. 5C illustrates a ~1 second digitally extracted segment of the whole sperm trajectory of FIG. 5B. The inset image represents the front-view of the "straightened" trajectory of the sperm. This motion is helical.

FIG. 5D illustrates a ~1 second digitally extracted segment of the whole sperm trajectory of FIG. 5B. The inset image represents the front-view of the "straightened" trajectory of the sperm. This motion is hyper-activated.

FIG. 9A illustrates a chiral ribbon pattern displayed by horse sperm trajectories taken over a duration of 4.6 seconds. Inset image represents lateral displacement of the straightened sperm trajectory (front view). The arrows indicate the directions of the sperms' forward movement.

FIG. 9B is a digitally zoomed segment (~0.7-sec long each) of the ribbon trajectory of FIG. 9A. The trajectory has left-handed twisting and form left-handed helical ribbons. Inset image represents lateral displacement of the straightened sperm trajectory (front view). The arrows indicate the directions of the sperms' forward movement.

FIG. 9C is a simulated trajectory that was generated by equation 2 herein to match the measured chiral ribbon trajectory of FIG. 9A.

FIG. 9D illustrates a chiral ribbon pattern displayed by horse sperm trajectories taken over a duration of 4.6 seconds. Inset image represents lateral displacement of the straightened sperm trajectory (front view). The arrows indicate the directions of the sperms' forward movement.

FIG. 9E is a digitally zoomed segment (~0.7-sec long each) of the ribbon trajectory of FIG. 9D. The trajectory has left-handed twisting and form left-handed helical ribbons. Inset image represents lateral displacement of the straightened sperm trajectory (front view). The arrows indicate the directions of the sperms' forward movement.

FIG. 9F is a simulated trajectory that was generated by equation 2 herein to match the measured chiral ribbon trajectory of FIG. 9D.

FIG. 10A illustrates a 5.0-sec long 3D trajectory showing the transitions between different swimming patterns of a horse sperm. This trajectory switched from a right-handed chiral ribbon pattern to a simple planar swimming pattern when the sperm encountered the bottom glass surface of the sample holder.

FIG. 10B illustrates a digitally zoomed ribbon segment (~0.7 seconds long) of the portion of the trajectory illustrated from FIG. 10A. The inset represents the lateral displacement of the straightened sperm track segment (front view). The arrows indicate the directions of the sperm's forward movement.

FIG. 10C illustrates a digitally zoomed planar segment (~0.7 seconds long) of the portion of the trajectory illustrated from FIG. 10A. The inset represents the lateral displacement of the straightened sperm track segment (front view). The arrows indicate the directions of the sperm's forward movement.

FIG. 10D illustrates a digitally zoomed ribbon segment (~0.7 seconds long) of the portion of the trajectory illustrated from FIG. 10A. The inset represents the lateral displacement of the straightened sperm track segment (front view). The arrows indicate the directions of the sperm's forward movement.

FIG. 11A illustrates a graph of VCL vs. VSL for 2625 ribbon tracks.

FIG. 11B illustrates LIN vs. ALH for 2625 ribbon tracks.

FIG. 11C illustrates RTW vs. VSL for 2625 ribbon tracks.

FIG. 12A illustrates an irregular trajectory of horse sperm.

FIG. 12B illustrates a linear trajectory of horse sperm.

FIG. 12C illustrates a planar trajectory of horse sperm.

FIG. 12D illustrates a helical trajectory of horse sperm.

FIG. 12E illustrates a ribbon trajectory of horse sperm.

FIG. 12F illustrates a hyper-activated (hyper-progressive) trajectory of horse sperm.

DETAILED DESCRIPTION OF THE ILLUSTRATED EMBODIMENTS

Figure 1A:
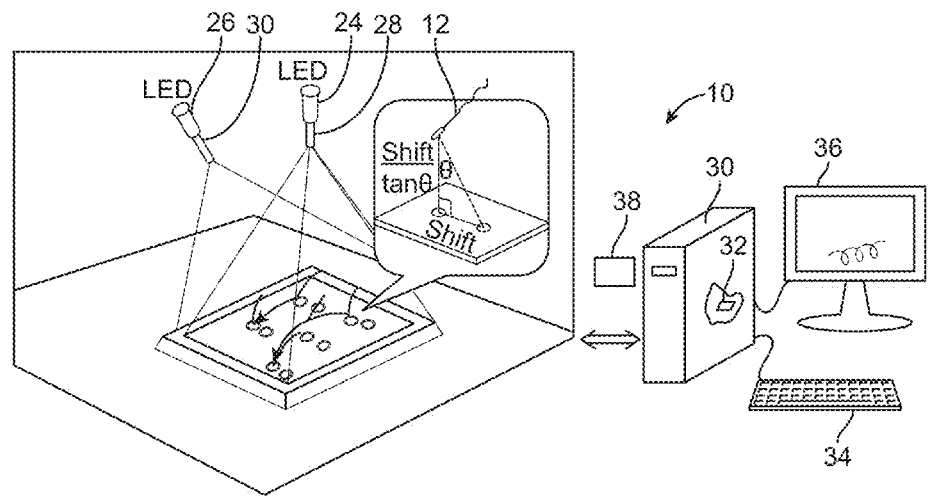
FIG. 1A illustrates a system for the three-dimensional imaging of motile objects contained within a sample according to one embodiment.

FIG. 1A illustrates a system 10 for the three-dimensional imaging of motile objects 12 contained within a sample according to one embodiment. A motile object 12 is an object that moves in one or more directions within a carrier fluid. A motile object 12 may include a microorganism or a cell. For example, in one embodiment, the motile object 12 comprises a sperm. The sperm may include human sperm or animal sperm (e.g., equine sperm). Typically, though not always, the motile object 12 may move because of a tail or flagella or cilia that move the object within a fluid environment. FIG. 1A illustrates a human sperm as the motile object 12. As seen in FIG. 1A, the system includes an image sensor 14. The image sensor 14 may include a CMOS sensor chip. The image sensor 14 may include a CMOS sensor chip such as the monochrome Aptina MT9P031STC (5 megapixels, 2.2 μm pixel size).

Figure 1B:
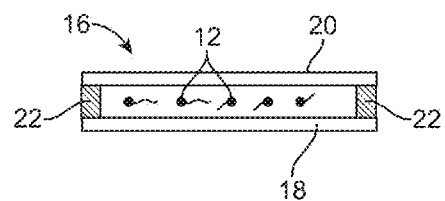
FIG. 1B illustrates a sample holder according to one embodiment.

The motile objects 12 are contained within a sample holder 16 as illustrated in FIG. 1B. The sample holder 16 defines a three dimensional volume (e.g., a chamber) that is able to hold a fluid containing the motile objects 12. The dimensions of the sample holder 16 may vary but it generally may occupy the general footprint of the image sensor 14. The sample holder 16 includes an optically transparent bottom 18 and top 20 that are separated from one another by a spacer 22. The optically transparent bottom 18 and top 20 may be formed of glass, plastic, or the like. The spacer 22 may include a cut piece of film or tape that is used to form the three-dimensional volume. The sample holder 16 may be designed as a disposable unit or reusable. The sample holder 16 is loaded atop the image sensor 14, for example, by placing the sample holder 16 directly on top of the glass cover of the image sensor 14. The sample holder 16 may substantially cover the entire FOV of the image sensor 14 or in some instances may be smaller than the entire FOV of the image sensor 14. For example, the sample holder 16 may be several millimeters in width and length (e.g., 3.5 mm width and 5.0 mm long). The sample holder 16 may have a depth of field (where the fluid resides) of around 0.01 mm to around 5.0 mm although other dimensions are contemplated (e.g., around 0.5 mm to around 1.0 mm) It is noteworthy that this depth is much larger than conventional sample holders that are used in connection with lens-based optical devices.

Referring back to FIG. 1A, the system 10 includes a first illumination source 24 and a second illumination source 26. Both the first illumination source 24 and the second illumination source 26 are located in different locations and are configured to illuminate the sample holder 16 (and motile objects 12 therein) from different angles. Both the first illumination source 24 and the second illumination source 26 are butt-coupled to respective multi-mode fibers 28, 30 (e.g., 0.4 mm core diameter fibers) that are oriented relative to each other to effectuate the illumination of the sample holder 16 at different angles. Single-mode optical fibers may also be used. For example, the first illumination source 24 may be oriented with respect to the sample holder 16 (or image sensor 14) at an angle of 0° while the second illumination source 26 may be oriented with respect to the sample holder 16 (or image sensor 14) at an angle of 45°. It should be understood that the particular angles may vary, what is important is that there is some angular offset between the first and second illumination sources 24, 26. A typical range of angles may be within the range of about 20° to about 60°. The light emitting ends of the respective multi-mode fibers 28, 30 may be located several centimeters (e.g., 10 cm) away from the sample holder 16.

Still referring to FIG. 1A, the first illumination source 24 and the second illumination source 26 emit light at different wavelengths according to one preferred embodiment. In one embodiment, the first and second illumination sources 24, 26 may include different color LEDs. For example, first illumination source 24 may comprise a red LED (e.g., 625 nm) while the second illumination source 26 may comprise a blue LED (e.g., 470 nm). While red and blue LEDs have been described it should be understood that different colors may also be used besides those specifically discussed herein. Further, it is possible to use first and second illumination sources 24, 26 emitting light at the same wavelength though different wavelengths or colors is preferable. As seen in the inset image of FIG. 1A, the first illumination source 24 and the second illumination source 26 create different holographic shadows at different locations on the image sensor 14. In the example of FIG. 1A, the first illumination source 24 creates a holographic shadow directly under where the motile object 12 is located. The second illumination source 26 creates a holographic shadow that is laterally shifted relative to the location of the motile object 12.

The first illumination source 24 and the second illumination source 26 may simultaneously illuminate the motile objects 12 within the sample holder 26 in one embodiment of the invention. Alternatively, the first illumination source 24 and the second illumination source 26 may be sequentially illuminated (i.e., source 24 ON/source 26 OFF followed by source 24 OFF/source 26 ON).

Still referring to FIG. 1A, the system 10 includes a computer 30 that is operatively coupled to the image sensor 14, first illumination source 24, and the second illumination source 26. The computer 30 may control the illumination of the illumination sources 24, 26. The computer 30 includes therein one or more processors 32 that are used to run software therein. The computer 30 may run common laboratory software such as LabView or the like. Also shown attached to the computer 30 are a keyboard 34 or other input device as well as a monitor 36. As seen in FIG. 1A, a power relay 38 may be connected to the computer 30 as well as the image sensor 14 to selectively power ON/OFF the image sensor 14. The power relay 38 may be programmed or otherwise controlled by the computer 30. Because the image sensor 14 generates heat which may be translated to the sample holder 16, in some embodiments, it is desirable to turn the image sensor 14 off between video acquisition sessions. The computer 30 can be used to control the turning ON/OFF of the sample holder 16 so that the temperature within the sample holder 16 is held to within a range of a target temperature (e.g., +/−5° C.). Alternatively, an optional heat sink (not shown) or other active cooling element may be used to wick heat away from the image sensor 14 and/or sample holder 16 in order to maintain a stable temperature therein. An active cooling element may include, by way of example, a thermoelectric cooler or the like.

The computer 30 is also used for data acquisition and processing. The image sensor 14 generates image frames taken of the motile objects 12 in the sample holder 16. These image frames are then transferred to the computer 30 for data processing. For example, the holographic shadow images are digitally process to reconstruct a projection image of each motile object for the first and second illumination source 24, 26. As described herein, the computer 30 also executes software instructions to identify the x, y, and z coordinates of the motile objects in each image frame based on the digitally reconstructed projection images of the mobile objects obtained from the first and second illumination sources 24, 26. The computer 30 is also used to connect the computed x, y, and z positions over a plurality of frames to form a three-dimensional track of the motile objects 12. Finally, the computer 30 via software executed on the at least one processor 32 is also used to automatically classify various three-dimensional tracks that are created by the motile objects 12. Exemplary three-dimensional tracks include, immotile, typical, helical, ribbon, hyper-ribbon, hyper-activated, and hyper-helical. The ribbon category may be further broken down to additional sub-categories of a chiral ribbon, helical ribbon, or twisted ribbon.

The computer 30 is programmed to capture several regions of interest (ROI) form the sample holder 16. The frame rate of the image acquisition system may vary depending, for example, on the beat frequency of the motile objects 12. For example, equine sperm have a higher beat cross frequency as compared to human sperm and thus may require a higher frame rate. The number of ROIs may also vary depending on the nature of the motile objects 12 being imaged. Human sperm, for instance, may require a lower number of ROIs (e.g., 16) while equine sperm may require more ROIs (e.g, 50).

Figure 2:
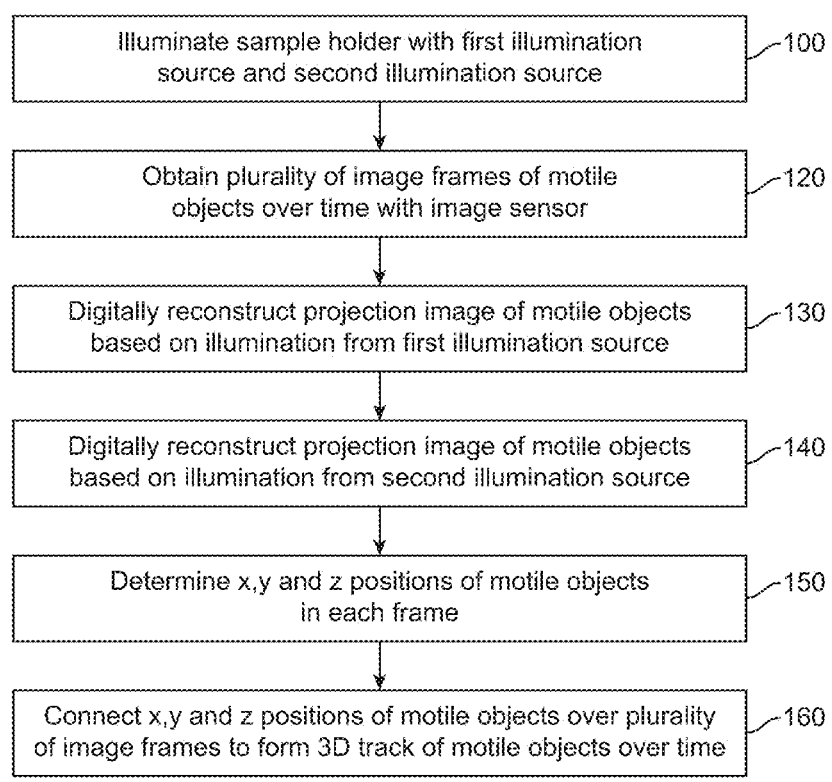
FIG. 2 illustrates a method for three-dimensional imaging of motile objects as a function of time according to one embodiment.

With reference to FIG. 2, an exemplary method is described for the three dimensional tracking of motile objects 12 contained within a sample. As best seen in operation 100, the sample holder 16 containing the motile objects 12 is illuminated with the first illumination source 24 and the second illumination source 26 wherein the first illumination source 24 and the second illumination source 26 are located at different positions from one another and emit light at different wavelengths. In one aspect of the invention, the first illumination source 24 and the second illumination source 26 illuminate the motile objects 12 simultaneously. However, in some alternative embodiments, the first illumination source 24 and the second illumination source 26 may illuminate the motile objects 12 sequentially. In operation 120, a plurality of image frames of the motile objects 12 over time are obtained with the image sensor 14 disposed adjacent to the sample holder 16 while the sample holder 16 is illuminated. In operation 130, a projection image of the motile objects 12 is digitally reconstructed in each frame based on illumination originating from the first illumination source 24. In operation 140, a projection image of the motile objects 12 is digitally reconstructed in each frame based on illumination originating from the second illumination source 26. As seen in operation 150, the x, y, and z positions of the motile objects 12 in each frame are identified based on the digitally reconstructed projection images of the mobile objects 12 obtained from the first and second illumination sources 24, 26. As seen in operation 160, the x, y, and z positions of the motile objects 12 are connected over the plurality of frames to form a three-dimensional track of the motile objects 12 within the sample.

Because the spatial information of each motile object 12 (e.g., sperm) is encoded with different wavelengths at two viewing angles, only the reconstruction that is performed with the correct combination of distance (i.e., depth), angle, and wavelength can generate clear images of the motile objects 12. In the case of sperm as the motile objects 12, because incorrectly reconstructed projection holograms of the sperm would only show up as weak background noise, the sperm head images projected in two different viewing angles at two different wavelengths can be isolated from each other although they were recorded at the same lens-free holographic frame. This provides an important solution to avoid confusing different projections of different sperms with each other, especially at high sperm densities, making the 3D tracking algorithm quite robust. Furthermore, without the need to record different viewing angles separately, this multicolor approach also simplifies the system, eliminating the use of pulsed light sources, high-speed digital cameras, and the synchronization between them.

Note that in the case of sperm as the motile objects 12, it should be emphasized that the swimming sperm tails do not constitute a problem in the localization calculations since they are considerably narrower (≤0.6 µm) compared to the sperm head (approximately 3-4 µm wide) and exhibit very weak light scattering, which significantly decreases their holograms' strength compared to the sperm heads' holograms. This behavior is also confirmed by the fact that the swimming sperm tails do not appear in the reconstructed amplitude images of the lens-free system.

In some circumstances, a digital cleaning step may be needed where there a lot of stationary objects (e.g., dead objects 12 or non-moving objects 12). In this optional cleaning step, each lens-free holographic frame is subtracted from a stationary image to remove the non-moving objects from the ROI. The stationary image may be generated by averaging consecutive lens-free image frames nearest to the processing frame in the video sequence of the same ROI.

The three-dimensional trajectories of motile objects inside the FOV of the image sensor 12 are reconstructed for each wavelength of the first and second illumination sources 24, 26. This digital reconstruction process for each illumination wavelength follows the iterative phase recovery method that is detailed, for example, in Isikman S. O. et al., Lens-free optical tomographic microscope with a large imaging volume on a chip, Proceedings of the National Academy of Sciences (PNAS), vol. 108, no. 18, 7296-7301 (2011), which is incorporated by reference herein. Reference is also made to International Patent Publication No. WO 2012/094523 which is also incorporated herein by reference.

In the digital reconstruction process, Fourier-projection theorem permits reconstruction of the three-dimensional transmission function of an object from two-dimensional projections along different directions. Reconstructed lens-free projection images are used to compute three-dimensional tomograms of the motile objects 12 using a filtered back-projection algorithm. In the context of sperm as the motile objects 12, the vertical and oblique lens-free projections of each sperm head are digitally reconstructed on all the possible depth (i.e., z) planes individually. In each reconstructed lens-free frame, possible sperm candidates were segmented by thresholding the amplitude image for both color channels. Detection artifacts were filtered out with a series of morphological criteria, such as peak value, area, and eccentricity. Once confirmed as the projection of a sperm, the 2D centroid position of each sperm projection in both color channels was calculated by its center-of-gravity based on the square of its reconstructed amplitude profile. At the same time, the focal distance of each vertical projection (which was estimated as the distance with the highest contrast in its reconstructed 2D image stack) was taken as the 'coarse' vertical (i.e., z) distance of the sperm from the CMOS sensor chip. This initial estimate has a lower depth accuracy of 5~10 μm and is just used to search for the corresponding projection of each sperm in the oblique illumination channel.

The x and y coordinates of the sperms were taken directly from the centroid positions of the vertical head projections, while the z (depth) coordinates of the sperms were calculated by dividing the distance between their vertical and oblique projection centroids with the tangent of the oblique illumination angle in water. A space-time matrix containing the spatial and temporal coordinates of all the sperms within the observation volume was generated by repeating the same 3D localization procedures depicted above on all the holographic frames. Finally, the 3D trajectory of each sperm was constructed by linking the detected points across the reconstructed 3D amplitude frames. To improve tracking accuracy, a Brownian-statistics-based algorithm was used such as that disclosed in Crocker, J. C. & Grier, D. G., Methods of Digital Video Microscopy for Colloidal Studies. J. Colloid Interface Sci. 179, 298-310 (1996), which is incorporated herein by reference.

Note that the shapes of the sperm heads are assumed to be either spherical or ellipsoidal so that the orientation of the heads will not create a systematic error in the centroid-based position estimation. For tracking of sperms with deformed heads, processing techniques like those reported in Memmolo, P. et al., On the holographic 3D tracking of in vitro cells characterized by a highly-morphological change, Opt. Express 20, 28485-28493 (2012), which is incorporated by reference, can potentially be used to minimize such errors and improve the reliability of the lens-free 3D tracking technique for deformed sperms.

After the construction of the 3D trajectories for the motile objects 12, the computer 30 can then automatically classify the trajectories into one of a plurality of categories. For example, the computer 30 may process data from a number of operations or procedures including, reconstruction of lens-free holographic images, localization of sperms' 3D centroids, tracking sperms' motion, and classification of their 3D swimming patterns. Algorithms may be stored or implemented using commercial software such as Matlab programs. The typical computation time for automatic processing of, e.g., approximately 1,600 lens-free images from a single semen sample is approximately 2.2 h (using Matlab R2011a running on a PC with an eight-core Intel Core i7-930 2.80 GHz processor). Since most of these procedures are highly repetitive and parallelizable, this computation time can be significantly shortened (by >5-10×) using graphics processing units (GPUs).

Experimental Data #1-3D Tracking of Human Sperm

The lens-free holographic frames recorded by the dual-view and dual-color lens-free holographic imaging set-up as described with respect to FIG. 1A. The sample holder containing the sperm suspension is placed directly on top of the protective glass of a Complementary Metal-Oxide-Semiconductor (CMOS) image sensor (Aptina MT9P031STC, 5 megapixels, 2.2 μm pixel size, monochrome) creating a physical distance of approximately 0.8 mm between the bottom of the sample holder and the top surface of the CMOS sensor active area. The sample suspension is simultaneously illuminated by two partially-coherent light sources with different central wavelengths placed at 45° with respect to each other (vertical one: 625 nm; oblique one at 45°: 470 nm). Both light sources were composed of light-emitting-diodes (LEDs, bandwidth approximately 20 nm) that were butt-coupled to multimode optical fibers (core size: 0.4 mm) with the fiber tips placed at a distance of approximately 10 cm from the sample holder. Such a system, without utilizing any lenses or mechanical scanners, can simultaneously record in-line holograms of the sperms from two different viewing angles over a large field-of-view, e.g., >20 $mm^2$, while also significantly reducing unwanted noise terms such as speckle patterns, multiple reflection interference noise or cross-interference among sperms' holograms. To capture the dynamics of the sperms with minimum motion blur, the electronic shutter of the CMOS image sensor was set to 5 ms for defining the integration time of each pixel. The FOV of the CMOS imaging platform (i.e., 24 $mm^2$) was digitally programmed into 16 regions-of-interest (ROIs), which were sequentially recorded at a frame rate of 92 frames per second (FPS) for continuous intervals of approximately 1-20 s each. The resulting video data were transmitted to a PC in real time through a gigabit Ethernet connection. To avoid the heating of the image sensor between tracking experiments, which might damage the sperms inside the sample holder, a programmable power relay (connected to the PC through a USB interface) was used to cut off the power of the image sensor between video acquisitions. The ON-OFF cycle of the image sensor was carefully configured to maintain the sample holder at 36-37° C. for several hours. A custom-designed LabVIEW program was used to coordinate the image sensor and the power relay for maintaining the temperature as well as to digitally scan over the 16 ROIs of the sample holder. Scanning over 16 ROIs (with >1,600 lens-free holograms) and recording the trajectories of >1,500 sperms takes approximately 10 min for each semen sample. However, this acquisition time can be significantly reduced to approximately 30 s if external cooling is provided to prevent the overheating of the sample holder.

Fresh semen specimens within less than 1 h after collection (from anonymous donors) were obtained from California Cryobank without preprocessing. Only specimens with high sperm concentration (>50×106 sperms per mL) and high motility (>70% motile) were used in the experiments. The motile sperms were first separated from seminal plasma by centrifugation with density gradient media (ISolate, Irvine Scientific) and then washed twice with artificial human tubal fluid (HTF, Sperm Washing Medium, Irvine Scientific) to completely remove the residue of seminal plasma. After the second washing step, the sperms were re-suspended with various culture media in centrifuge tubes at a concentration of approximately $10 \times 10^6$ sperms per mL and incubated at 37° C. with pH buffer Hepes until the imaging measurements.

Three different culture media were used in this work: (i) Baseline medium, which only contained artificial HTF; (ii) suppressing medium I, which was prepared by mixing seminal plasma with HTF by a ratio of 1:9; and (iii) suppressing medium II, which was prepared by mixing seminal plasma with HTF by a higher ratio of 2:8. For all imaging experiments except the time-traced ones, the sperm suspensions were incubated for approximately 2-3 h. Right before lens-free imaging experiments, approximately 50-150 µL of the sperm suspension was put into a disposable sample holder prepared by taping a laser-cut Acetal film (approximately 0.1-0.5 mm thick) between two pieces of No. 1 cover slips.

FIGS. 3A-3D illustrate the digital separation of the sperms' vertical and oblique lens-free projections through dual-angle and dual-color partially-coherent illumination. More specifically, FIG. 3A illustrates the lens-free image showing several sperm holograms recorded with a red LED at the vertical angle and a blue LED at the oblique angle simultaneously illuminating the sample. FIGS. 3B through 3E illustrate lens-free images that were digitally reconstructed from the same region of interest shown in FIG. 3A, but each with the conditions specified in its respective legend. The triangles in FIG. 3B mark the successful detection of the vertical projections of the sperms, whereas the circles in FIG. 3E label the successful detection of oblique projections. Reconstruction with parameters that are not matched to the original illumination conditions would only create weak noise at the background as illustrated in FIGS. 3C and 3D.

The 3D swimming patterns of human sperms were automatically categorized based on several dynamic parameters extracted from their reconstructed 3D-t (space-time) trajectories, such as curvilinear velocity, linearity, lateral displacement, and number of stable turns (rotations. To quantify the 3D trajectories of human sperms with parameters that are compatible with the currently existing standards, the parameters were modified that are used by computer-aided sperm analysis (CASA) systems, which can be summarized as below:

i. Straight-line velocity (VSL) is defined as the distance between the first and the last position points in the track segment of a sperm trajectory divided by the total duration of the track segment (unit: µm/sec).

ii. Curvilinear velocity (VCL) is defined as the sum of the distances between every two consecutive position points in a track segment divided by the total duration of the track segment (unit: µm/sec).

iii. Linearity is the ratio between straight-line velocity and curvilinear velocity (VSL/VCL) of a track segment (unit: none).

iv. Amplitude of lateral head displacement (ALH) is defined as twice the maximum displacement of a sperm head from its fitted moving axis in a track segment (unit: mm). It is directly related to the level of bending in the proximal region of the tail (i.e., a larger ALH value corresponds to stronger bending).

v. Beat-cross frequency (BCF) is defined as the frequency that the sperm head moves across the middle plane of the "straightened" trajectory (unit: Hz). The middle plane is determined as the plane in the $X_r$-$Y_r$-$Z_{ax}$ space that contains the central axis $Z_{ax}$ and has the most frequent crossing-over of the sperm head. The value of BCF is in general sub-linearly proportional to the beating frequency of the sperm tail and is roughly double the frequency of head wobbling.

vi. Rotation speed (RPS) is defined as the slope of the linear function that best fits the time evolution of the unwrapped rotation angle of a sperm head projected on the $X_r$-$Y_r$ plane (unit:revolutions per second, r/sec). It represents how fast a helical track segment revolves around its moving axis and is roughly half of the value of the trajectory's beat-cross frequency.

vii. Number of stable turns (NST) is defined by multiplying the rotation speed of a sperm with the duration that a track segment maintains a small error (≤0.6 radians in this study) to the fitted linear function in its unwrapped angle; unit:none. The segment with a small angle error needs to be longer than one rotation cycle for being counted into the number of stable turns. NST represents how close the track segment is to a bended helix and a value equal to or larger than 2 was chosen to qualify this track segment as a "helical sperm trajectory".

All the parameter extraction performed in this work was based on either 1.1 sec-long trajectories (~100 frames at 92 FPS) or track segments of such length that were digitally extracted from longer trajectories (e.g., 10-20 sec long). Before automatically extracting these dynamic parameters for each sperm within the observation volume, the reconstructed 3D trajectory segments need to go through a digital "straightening" process to compensate the curvature in their 3D motion. To this end, a 3D parabolic curve model was used to fit the curved moving axis of each segment by minimizing the square of the distance between all the position points and the fitted axis (where the distance was created by the sperm's lateral displacement). All the position points were then reassigned laterally onto a plane moving along the axial direction according to their relative position to the fitted axis. After this digital straightening step, the moving axis of each segment became a straight line and the position points evolved laterally around the fitted axis. The lateral coordinates of the position points were then used to calculate the instantaneous radius and the angle of the trajectory points, where the instantaneous angle was further unwrapped to eliminate possible $2\pi$ phase jumps and fitted with a linear function to estimate its rotation speed.

Note that in this work all the human sperm trajectories with a VCL that were smaller than 30 µm/sec were considered as immotile. The motile sperm trajectories that cannot be classified as helical, hyper-activated, or hyper-helical are then classified as 'typical' trajectories. For distinguishing helical, hyper-activated and hyper-helical 3D sperm trajectories from 'typical' ones, the following criteria have been used:

Helical trajectory—NST≥2.0.

Hyper-activated trajectory—VCL needs to be larger than 150 µm/sec; the linearity needs to be smaller than 0.5; and ALH needs to be larger than 7.0 µm.

Hyper-helical trajectory—All the requirements for both helical and hyper-activated trajectories need to be satisfied.

Because of the fact that the fitting of helices requires more than two stable turns and that the hyper-activated sperms can change their swimming patterns back and forth within a few seconds, longer sperm trajectories are digitally divided into track segments that are each ~1.1 sec long, which is long enough for fitting a helix but short enough for minimizing swimming pattern transitions within each segment.

Results

Figure 4A:
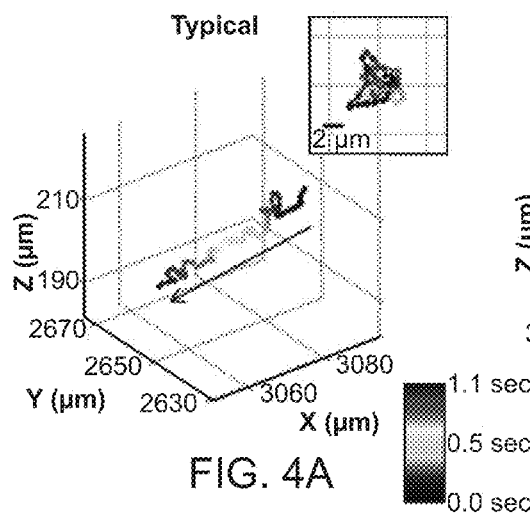
FIG. 4A illustrates the typical human sperm swimming pattern. The inset image represents the front-view of the "straightened" trajectory of the sperm. Arrows indicate direction of forward movement of sperm.

Human sperms exhibit a large variation in their 3D swimming patterns, and therefore using the dual-view lens-free holographic imaging platform (FIG. 1A), these swimming patterns were initially grouped into four major categories as exemplified in FIGS. 4A-4D (i.e., typical, helical, hyper-activated, and hyper-helical). The 'typical' trajectory is shown in FIG. 4A is the most prevalent swimming pattern observed among human sperms (>90%), in which the sperm head moves forward swiftly (as fast as e.g., 140 μm/sec) along a slightly curved axis with a small lateral displacement (e.g., ~4 μm side-to-side). In this category (i.e., 'typical'), although the lateral displacement exhibits a certain degree of periodicity, the sperm head changes its direction arbitrarily in 3D space. However, when these typical trajectories are located near the sample holder boundaries, some of them also exhibit lateral displacements that are better confined to a two dimensional plane which is not necessarily parallel to the boundary.

Figure 4B:
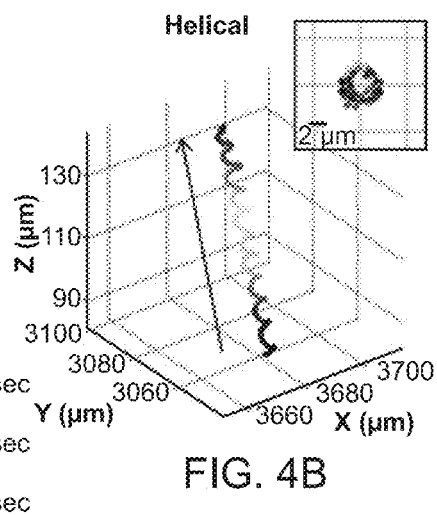
FIG. 4B illustrates the helical human sperm swimming pattern. The inset image represents the front-view of the "straightened" trajectory of the sperm. Arrows indicate direction of forward movement of sperm. The helices are right-handed.

In the second category of swimming patterns that human sperms exhibit, helical trajectories were observed (~4-5% of motile human sperms) as exemplified in FIG. 4B), which show the sperm head moving forward with very stable revolutions around a central axis, creating a well-defined helix. Not only this helical trajectory (e.g., FIG. 4B) is quite tight with an average helix radius of e.g., ~1.7 μm and a rotation speed of e.g., ~10 rotations/sec, but also it moves rather fast traveling more than e.g., 30-40 μm in depth-of-field (i.e., z direction) within ~4 sec making it rather challenging to observe with a typical objective-lens due to its limited depth-of-field and observation volume. In contrast to 'typical' swimming patterns, it was observed that the structure of these helical patterns did not alter much when the sperm head was near the boundaries of the sample holder.

Figure 4C:
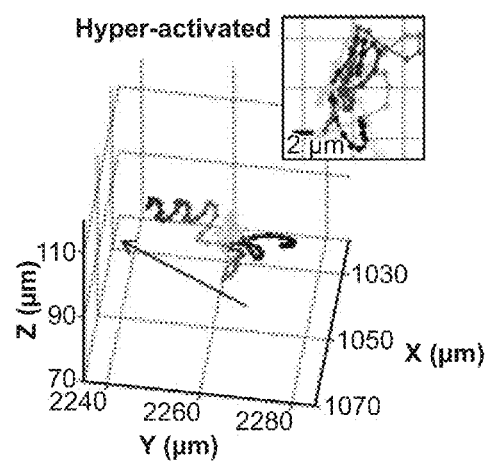
FIG. 4C illustrates the hyper-activated human sperm swimming pattern. The inset image represents the front-view of the "straightened" trajectory of the sperm. Arrows indicate direction of forward movement of sperm.
Figure 4D:
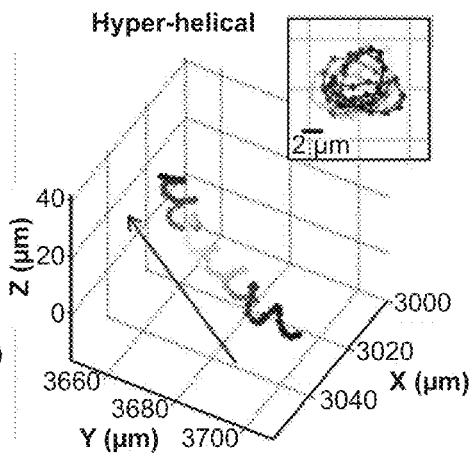
FIG. 4D illustrates the hyper-helical human sperm swimming pattern. The inset image represents the front-view of the "straightened" trajectory of the sperm. Arrows indicate direction of forward movement of sperm. The helices are right-handed.

In the third category, observed hyper-activated 3D swimming patterns were observed (≤3% of motile human sperms) that exhibit quite different movement compared to the previous two pattern types (see e.g., FIG. 4C). The most noticeable change in a hyper-activated pattern is the decrease of its forward movement, despite the fact that the instantaneous speed of hyper-activated sperms (e.g., >150 μm/sec) is usually 2× faster than the instantaneous speed of 'typical' or 'helical' sperms. Most of the track length of a hyper-activated human sperm is consumed by the increased lateral movement, which has a size of >7 μm from one side to the other (see e.g., FIG. 4C). This hyper-activated swimming pattern can be also divided into two sub-categories, similar to 2D observations: (i) transitional hyper-activation, where the sperm still moves forward with a "meander" track (see e.g., FIG. 4C); and (ii) "star-spin" hyper-activation (mostly observed near the sample holder boundaries), where the sperm bounces around vigorously but totally loses its forward movement. Similar to the 'typical' swimming patterns, many of the sperms in transitional hyper-activation category show quasi-2D lateral displacement near the sample holder boundaries.

In the final category of human sperm swimming patterns, hyper-helical patterns were observed (see e.g., FIG. 4D) which can be considered as a combination of transitional hyper-activation and regular helical trajectories, exhibiting enlarged and slightly more unstable revolutions around a helix axis with a sustained forward movement. This swimming pattern was significantly rare, constituting only <0.5% of motile human sperms. No major difference in swimming patterns was observed between the hyper-helical trajectories located in free 3D volume and the ones located near the sample holder boundaries. Table 1 below illustrates the relative ratios of different swimming patterns.

TABLE 1

|  | Typical | Helical | Hyper-activated | Hyper-helical |
| --- | --- | --- | --- | --- |
| Mean | 92.9% | 4.4% | 2.5% | 0.2% |
| Standard Deviation | ±5.3% | ±1.5% | ±1.3% | ±0.2% |

These patterns were observed in 28 measurements of six semen specimens from different donors, containing 24,090 motile human sperms. The standard deviations listed in parentheses were obtained by calculating the deviation of each ratio observed across all the 28 measurements. These measurements were made in baseline medium (artificial HTF) after >2 h of incubation.

An important feature of the lens-free on-chip imaging approach is that it can track 3D trajectories of >1,500 human sperms over a large sample volume, which enables one to observe the transitions among different swimming patterns across a time window of ~10-20 sec for each continuous sperm trajectory. FIGS. 5A-5D illustrate examples of such swimming pattern transitions acquired using the lens-free imaging platform. FIG. 5B illustrates a 10.9-sec long trajectory showing the transitions between different swimming patterns of a human sperm. FIGS. 5A, 5C, and 5D illustrate digitally extracted segments (~1-sec long each) of the whole sperm trajectory shown in FIG. 5B. The inset in each panel is the front-view of the "straightened" trajectory of the sperm.

Based on the measurement results, Table 2 below summarizes the statistics of such transitions among different swimming patterns observed in human semen samples. These results reveal that most of the observed helical and hyper-activated trajectories quickly switch back to 'typical' swimming patterns (e.g., ~64% for helical trajectories and ~58% for hyper-activated trajectories).

TABLE 2

|  | Typical - To | Helical - To | Hyper-activated - To | Hyper-helical - To |
| --- | --- | --- | --- | --- |
| Typical - From | 85.1% (±8.1%) | 10.1% (±7.0%) | 4.8% (±4.1%) | 0.0% (±0.0%) |
| Helical - From | 63.8% (±25.0%) | 30.0% (±22.1%) | 5.0% (±10.3%) | 1.3% (±3.6%) |
| Hyper-activated - From | 57.7% (±31.3%) | 2.1% (±4.7%) | 30.9% (±28.6%) | 9.3% (±9.2%) |
| Hyper-helical - From | 36.7% (±38.5%) | 13.3% (±30.7%) | 40.0% (±44.9%) | 10.0% (±30.3%) |

The relative percentage of swimming pattern transitions (From-To) observed within 3,473 segments (each approximately 1.1 s long) of 656 human sperms trajectories (each approximately 5.5-10.9 s long). The standard deviations in parentheses were obtained by randomly dividing the 656 trajectories into 16 groups and calculating the relative percentage deviation of each transition across these groups.

The human sperm tracking experiments can be further summarized in Table 3 below, where various parameters of 3D swimming patterns, e.g., curvilinear velocity (VCL), straight-line velocity (VSL), amplitude of lateral head displacement (ALH), beat-cross frequency (BCF), linearity are quantified and compared to the statistical behavior of only the helical human sperms, which constitute <5% of the motile sperms. The mean values of these swimming parameters and their standard deviations are also listed in Table 3.

TABLE 3

| | Straight-line velocity (VSL) (μm/sec) | Curvi-linear velocity (VCL) (μm/sec) | Linearity (VSL/VCL) | Lateral Head Displacement (ALH) | Beat-cross frequency (BCF) (Hz) |
|---|---|---|---|---|---|
| Mean | 55.7 | 88.0 | 0.61 | 5.4 | 15.7 |
| Standard Deviation | ±24.9% | ±28.7% | ±0.21% | ±2.9% | ±5.1 |

Based on these results, it is rather interesting to note that a significant majority (~90%) of helical human sperms in baseline medium prefer right-handed helixes over left-handed ones, exhibiting a tight helix radius of e.g., 0.5-3 μm and a rotation speed of e.g., 3-20 revolutions/sec.

Figure 6:
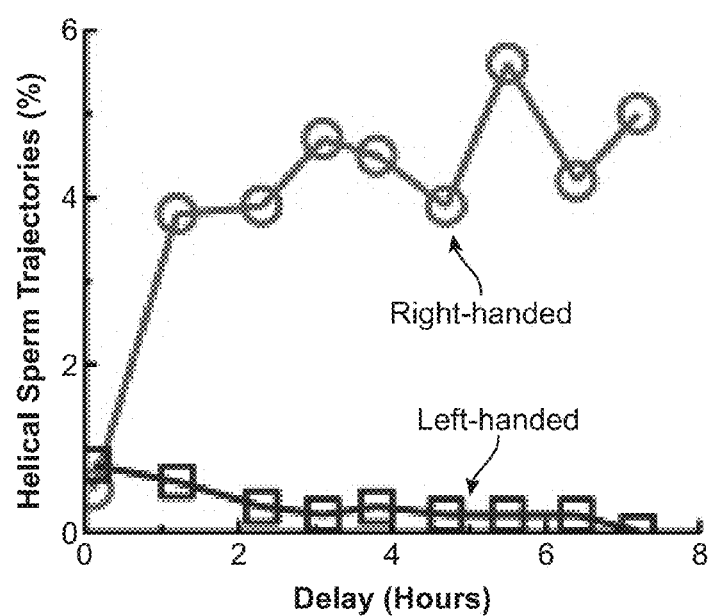
FIG. 6 is a graph of the time evolution of helical sperm trajectories after re-suspension in artificial human tubal fluid (HTF). After ~2-3 hours of incubation in HTF, the percentage of right-handed helical trajectories significantly increased to ~4-5% of motile human sperms, while the percentage of left-handed ones did not show a major change, remaining to be <0.5% of motile sperms.

To shed more light on this observation (i.e., the preference of right-handed helices), an additional experiment was performed (data shown in FIG. 6) to measure the percentage of helical trajectories as a function of time after the sperms were removed from seminal plasma and were placed into baseline medium. The results of this time-traced experiment revealed that, after removal of the seminal plasma, the percentage of right-handed helical sperms significantly increased within ~2-3 hours of incubation in baseline medium, reaching ~4-5% of motile human sperms (see FIG. 6). On the other hand, the same experiment did not reveal any major changes in the left-handed helical sperm percentage as a function of time, which remained to be <0.5% even after >3 hours of incubation in baseline medium as illustrated in FIG. 6.

Figure 7B:
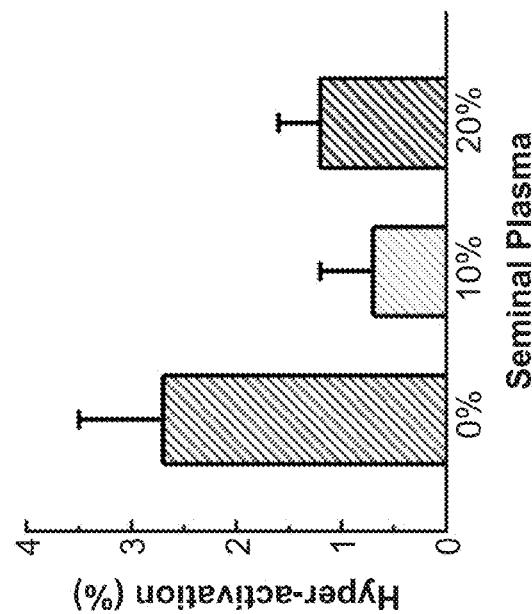
FIG. 7B illustrates the quenching of human sperm hyper-activated trajectories as a function of increased seminal plasma concentration in culture medial. Each of the mean±s.d. bars was based on 14 measurements of 2 specimens (7 with each) obtained from different anonymous donors.
Figure 7A:
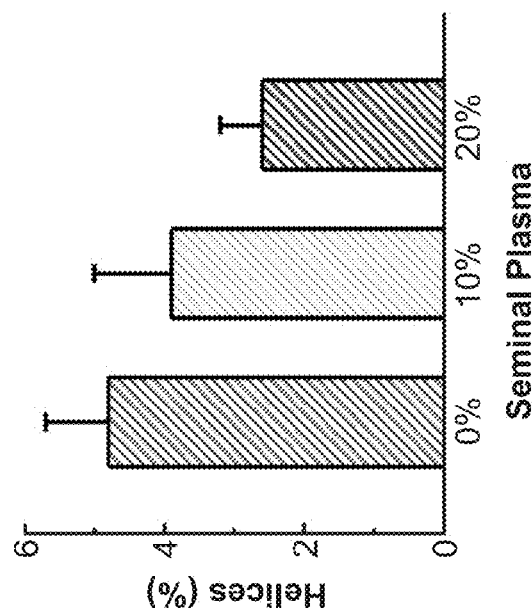
FIG. 7A illustrates the quenching of human sperm helical trajectories as a function of increased seminal plasma concentration in culture medial. Each of the mean±s.d. bars was based on 14 measurements of 2 specimens (7 with each) obtained from different anonymous donors.

These results also suggest that seminal plasma significantly suppresses helical trajectories of human sperms, while human tubal fluid initiates them. An experimental comparison of how different concentrations of seminal plasma affect the 3D swimming patterns of human sperms (in specific helical and hyper-activated trajectories) is also provided in FIGS. 7A and 7B, which once again confirmed the suppressing effect of seminal plasma on helical trajectories (after >2 hours of incubation time). Another important observation is that the helical trajectories, compared to the hyper-activated ones, were more difficult to suppress by increasing the percentage of seminal plasma in medium, suggesting that these two swimming patterns might be regulated through different mechanisms.

DISCUSSION

It should be emphasized that to obtain large statistics regarding the swimming patterns of human sperms one would need a high-throughput imaging platform with sub-micron 3D tracking accuracy and sub-12-ms temporal resolution to clearly resolve different patterns, especially the helical patterns, which exhibit a tight helix radius of e.g., ~0.5-3 μm with a fast rotation speed that might reach e.g., 15-20 rotations/sec. Conventional microscopes equipped with e.g., high-magnification objective lenses and high-frame-rate cameras can only meet these requirements for imaging sperms along a 2D plane, which can infer limited information on their natural 3D motion. Estimation of the 3D trajectories of sperms from their 2D observations can also be feasible in some cases by assuming a known swimming pattern. However, such approaches in general would not be able to infer the details and quantify the fine parameters of 3D sperm trajectories due to lack of position information along the third dimension. A 2D vs. 3D comparison of human sperm trajectories is provided in FIGS. 8A-8H to better illustrate that different swimming patterns of human sperms can look very similar in 2D observation while their 3D patterns are vastly different.

Figure 8A:
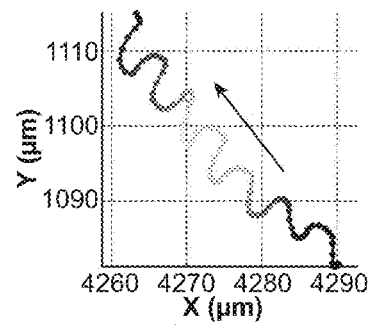
FIG. 8A illustrates the 2D tracking of planar sperm trajectories.
Figure 8B:
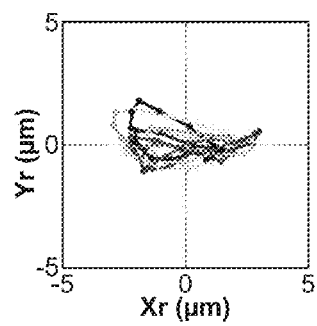
FIG. 8B illustrates the front-view of the straightened 3D trajectory of FIG. 8A.
Figure 8C:
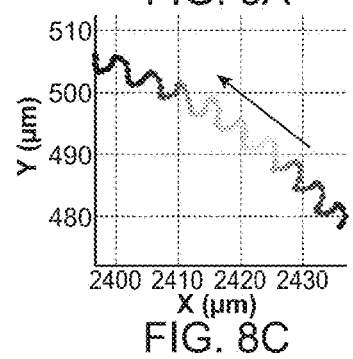
FIG. 8C illustrates the 2D tracking of planar sperm trajectories.
Figure 8D:
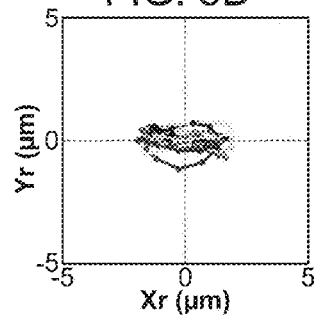
FIG. 8D illustrates the front-view of the straightened 3D trajectory of FIG. 8C.
Figure 8E:
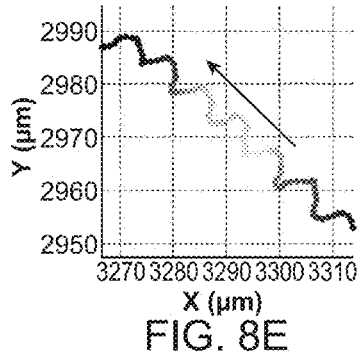
FIG. 8E illustrates the 2D tracking of helical sperm trajectories.
Figure 8F:
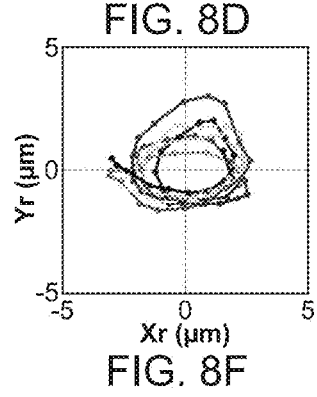
FIG. 8F illustrates the front-view of the straightened 3D trajectory of FIG. 8E.
Figure 8G:
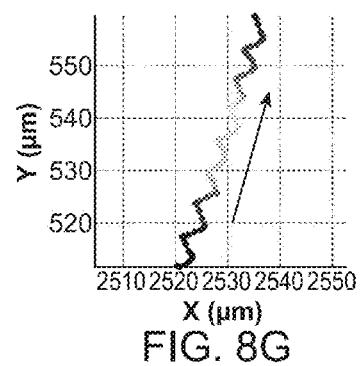
FIG. 8G illustrates the 2D tracking of helical sperm trajectories.
Figure 8H:
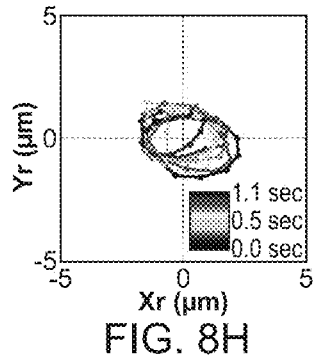
FIG. 8H illustrates the front-view of the straightened 3D trajectory of FIG. 8G.
Figure 13:
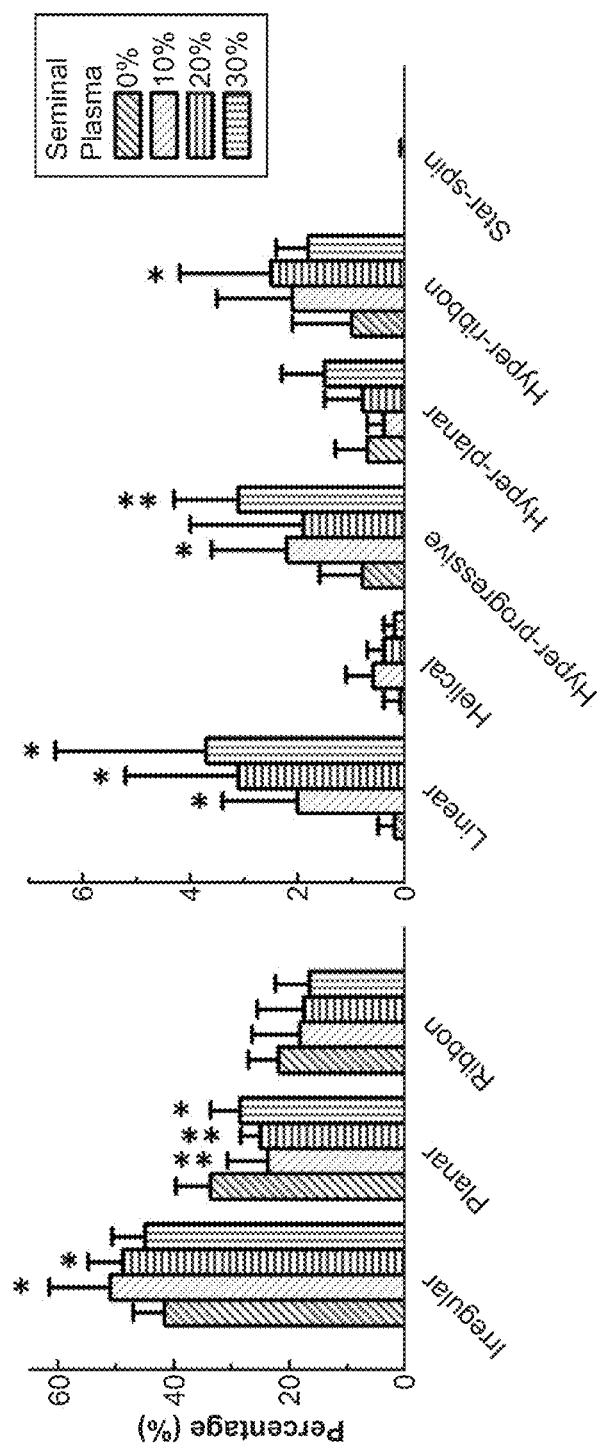
FIG. 13 illustrates the relative percentages of horse sperm swimming patterns as a function of the seminal plasma concentration in culture media. Each of the mean±SD bars was based on 8 measurements of 2 specimens (4 with each specimen). The statistics shown in FIG. 13 for planar and ribbon patterns do not include hyper-planar and hyper-ribbon trajectories, respectively. $*P<0.05$, $P<0.01$ and $*P<0.001$ (two-tailed Student's t-test in comparison with the plasma-free dataset).

FIGS. 8A and 8C illustrate 2D tracking of two planar sperm trajectories. FIGS. 8B and 8D show the front-views of the "straightened" 3D trajectories for FIGS. 8A and 8C, respectively. FIGS. 8E and 8G illustrate 2D tracking of two helical sperm trajectories. FIGS. 8F and 8H show the front-views of the "straightened" 3D trajectories for FIGS. 8E and 8G, respectively. As illustrated in this figure, unlike 3D imaging, 2D tracking of human sperms cannot differentiate planar and helical trajectories from each other.

In general, human sperm trajectories reconstructed by this 3D tracking technique are consistent with previous observations made by conventional lens-based 2D microscopy tools. Most sperms swim forward with quasi-periodic small lateral displacements, while some sperms move with enlarged lateral displacement (transitional hyper-activation), and some other sperms display the "star-spin" movement (complete hyper-activation). In addition to this, the extra depth information provided by the lens-free imaging technique enabled one to reconstruct the complete 3D trajectories of human sperms, isolating the helical motion from e.g., planar or other types of swimming patterns.

Furthermore, this approach also permits investigation of sperms' 3D distribution inside a sample holder, shedding more light on the effect of surface boundaries on 3D swimming patterns of human sperms. Similar to what was reported previously for sample holders that are deeper than a sperm's body length, the accumulation of human sperms on the inner surfaces of the sample holder was also observed in these experiments. Although such accumulation happens on both the top and bottom surfaces for all four swimming patterns, the presence of the surface boundaries only modifies the typical and hyper-activated patterns but not the helical ones. Note that in these experiments, plain glass surfaces were used without siliconization to prevent electrostatic adherence of sperms. With different surface treatment methods, the platform can also be used to study how the surface properties can affect the statistics of sperm movement.

Compared to the swimming patterns of e.g., sea urchin sperms, which have also been extensively studied, human sperms exhibit some distinct features in their 3D swimming behavior. First, motile human sperms, just like other mammalian sperms, occasionally display hyper-activated swimming patterns, however sea urchin sperms do not exhibit hyper-activation. Second, when swimming near a surface, sea urchin sperms tend to follow circular swimming paths with a strongly preferred handedness, whereas human sperms do not exhibit such behavior. Third, helical trajectories of human sperms can be observed both in free 3D volume and near solid surfaces; however sea urchin sperms only display helical movement in free 3D volume. Fourth, the helical trajectories of human sperms, compared to sea urchin sperms, exhibit significantly smaller helix radii (1.6±0.5 μm vs. 6.8±1.1 μm) and faster rotation speeds (6.8±4.6 r/sec vs. 4.0±0.8 r/sec), making them much more challenging to resolve in 3D.

Although large statistics on 3D trajectories of >24,000 human sperms are reported revealing several important observations that have so far been hidden due to limited capabilities of existing optical imaging platforms, most of the regulating mechanisms behind these observations still remain unclear. For example, in the experiments seminal plasma suppressed the percentage of helical sperm trajectories. This observation could be due to (1) the higher viscosity of seminal plasma; or (2) its chemical composition. The effect of medium viscosity to make helical movement unsustainable is also supported by previous studies, where high viscosity is shown to reduce the amplitude of sperms' lateral head displacement. However, the time lag (see FIG. 6) between the removal of human sperms from seminal plasma and the appearance of helical trajectories suggests that there should be some other bio-chemical factors involved, which delay the activation of this helical movement. By imaging human sperms in media with various activating or suppressing constituents, the 3D tracking platform can be used to better investigate the underlying mechanisms regulating such helical or hyper-helical patterns. Along the same lines, the lens-free sperm imaging platform can also provide a high-throughput tool to rapidly quantify the impact of e.g., various stimuli and drugs on the 3D swimming patterns of sperms.

The large statistics provided by this lens-free imaging platform reveal that only ~4-5% of the motile human sperms swim along well-defined helices and that this percentage can be significantly suppressed under seminal plasma. Furthermore, among these observed helical human sperms, a significant majority (~90%) preferred right-handed helices over left-handed ones, with a helix radius of ~0.5-3 µm, a helical rotation speed of ~3-20 rotations/sec and a linear speed of ~20-100 µm/sec. This high-throughput 3D imaging platform could in general be quite valuable for observing the statistical swimming patterns of various other micro-organisms besides sperm, leading to new insights in their 3D motion and the underlying bio-physics.

Experimental Data #2-3D chiral ribbon swimming patterns

This experiment discovered an entirely new three-dimensional (3D) swimming pattern that was observed in human and horse sperms. This motion is in the form of 'chiral ribbons', where the planar swing of the sperm head occurs on an osculating plane creating in some cases a helical ribbon and in some others a twisted ribbon. The latter, i.e., the twisted ribbon trajectory, also defines a minimal surface, exhibiting zero mean curvature for all the points on its surface. These chiral ribbon swimming patterns cannot be represented or understood by already known patterns of sperms or other micro-swimmers. The discovery of these unique patterns is enabled by holographic on-chip imaging of >33,700 sperm trajectories at >90-140 frames/sec, which revealed that only ~1.7% of human sperms exhibit chiral ribbons, whereas it increases to ~27.3% for horse sperms. These results shed more light onto the statistics and biophysics of various micro-swimmers' 3D motion.

Preparing and Incubating Sperm Suspension

Frozen sperm specimens of a Warmblood stallion were obtained from the Center for Equine Health at the University of California, Davis. Before freezing, fresh semen specimens were first diluted to a concentration of 50 million sperms per ml with equine semen extender (E-Z Mixin BFT, Animal Reproduction Systems) and then were centrifuged at 400G for 15 min. After centrifugation the pellet was re-suspended in freezing extender (E-Z Freezin Equine Semen Extender, Animal Reproduction Systems) with a final concentration of 400 million sperms per ml. The processed sperms specimens were packaged in 0.5 ml straws and frozen in a programmable freezer. When the straws had reached −150° C. they were plunged in liquid nitrogen for storage.

To prepare the horse sperm suspension for imaging, the frozen specimens were first thawed at 38° C. water bath for 30 sec, and then rehydrated for 15 min by mixing with equine semen extender (BotuSemen, Nidacon, Sweden) by a ratio of 1:1. After rehydration, gradient density centrifugation with isotonic density medium (Equipure, Nidacon, Sweden, 200 g for 30 min) was used to concentrate the motile sperms within the semen specimens. The centrifuged sperm pellet was re-suspended with the same equine semen extender at a concentration of ~1 million sperms per ml (>50% motile) and then incubated for another 30 min. Right before lens-free on-chip imaging experiments, ~25 µL of the sperm suspension was put into a disposable sample holder prepared by taping a laser-cut Acetal film (~0.15 mm thick) between two pieces of No. 1 cover slips.

Dual-View and Dual-Wavelength Lens-Free on-Chip Holographic Imaging and Tracking Set-Up A dual-view and dual-wavelength lens-free on-chip holographic imaging setup, as illustrated in FIG. 1A, was utilized to record the 3D movement of sperms. Two partially-coherent light sources (LED-coupled multimode fibers, core size: 400 µm) illuminated the sample holders from two different angles with two different wavelengths (vertical one: 625 nm; oblique one at 45°: 470 nm; bandwidth ~20 nm). When recording the 3D movement of sperms, the sample holder was placed directly on the top of the protection glass of a CMOS (Complementary Metal-Oxide-Semiconductor) image sensor (Aptina MT9P031STC, 5 mega-pixels, 2.2 µm pixel size, monochrome). The power of this image sensor chip was cut off between video acquisition sessions to maintain the temperature of the sperm sample holder at ~37-39° C.

The frame rate of the computational imaging system used was raised to 143 FPS to oversample the faster beating of horse sperms (beat-cross-frequency, BCF: ~30 Hz), whereas it was operated at ~92 FPS for imaging of human sperms. Such high frame rates reduced the imaging area of individual regions-of-interest (ROIs) that the CMOS image sensor chip can record at its full speed. Therefore, the whole field of view (FOV) of the image sensor was digitally divided into 16 (for human sperms) or 50 (for horse sperms) ROIs, which were sequentially recorded for continuous intervals of e.g., 0.7-7.0 seconds each. For horse samples, scanning over 50 such ROIs (with >5,000 lens-free holographic frames) and recording the 3D trajectories of >1,000 sperms took approximately 30 min for each semen sample. At the same time, the exposure time of the imaging system was also shortened to ~3 ms to avoid motion blur in recording the high-speed movement of horse sperms (which exhibit a typical instantaneous speed of e.g., ~150 µm/sec).

Reconstructing the 3D Trajectories of Sperms

For horse sperm, due to the high density of dead sperms and un-dissolved extender solute in the suspension liquid, each lens-free holographic frame was subtracted from a stationary image to remove the holograms of non-moving objects within the ROI. This stationary image was generated by averaging 100 consecutive lens-free frames that are nearest to the processing frame in the video sequence of the same ROI. These digital background cleaning steps were not needed and were not used for human sperm data.

The 3D trajectories of mobile sperm inside the FOV of the image sensor were then reconstructed as described previously. The vertical and oblique lens-free projections of each sperm head were digitally reconstructed on all the possible depth (i.e., z) planes individually. After passing through a morphological screening process, the centroid positions of both the vertical and the oblique sperm head projections were calculated by their centers-of-gravity within their corresponding reconstructed amplitude images. The x and y coordinates of the sperms were taken directly from the centroid positions of the vertical head projections, while the z (depth) coordinates of the sperms were calculated by dividing the distance between their vertical and oblique projection centroids with the tangent of the oblique illumination angle in water. A space-time matrix containing the spatial and temporal coordinates of all the sperms within the observation volume was generated by repeating the same 3D localization procedures depicted above on all the holographic frames. Finally, the 3D trajectory of each sperm was constructed by linking the detected points across the recorded frames by a Brownian-statistics-based algorithm. The shapes of the sperm heads are assumed to be either spherical or ellipsoidal so that the orientation of the heads will not create a systematic error in the centroid-based position estimation.

Definitions of Sperm 3D Dynamic Swimming Parameters

To quantify the 3D dynamics of sperm motion, a series of parameters were extracted from individual reconstructed sperm trajectories. All the parameters reported for horse sperms in this work were extracted from either 0.7 sec-long trajectories (~100 lens-free frames at 143 FPS) or track segments of such length that were digitally cropped from longer trajectories (e.g., ~4-7 sec long). For human sperms, however, these parameters were extracted from 1.1 sec-long tracks (~100 lens-free frames at 92 FPS). A digital "straightening" process was performed to compensate the curvature in sperm's forward motion before extracting these dynamical parameters. The definitions of parameters such as straight-line velocity (VSL), curvilinear velocity (VCL), linearity (LIN), amplitude of lateral head displacement (ALH) have been described previously. This work elaborates on the definition of the dynamical parameters that were newly introduced in this work:

Rate of twisting (RTW) represents the rotation speed (units: rad/sec) of the head beating plane for a sperm swimming in a ribbon pattern. It is defined as the angular frequency of the linear function that best fits the time evolution of the osculating plane angle for a track segment. The osculating plane angle on each position along the track segment is calculated by finding the most frequent angle of the lateral displacements occurring in the adjacent beating cycle, whose duration is defined by 2/BCF.

Twisting stability (TWS) is defined as the ratio between the accumulated angle change of the osculating plane and the averaged error to the best-fit linear function in the osculating plane angle. Both the angle change accumulation and the error averaging (by taking root mean square) were performed across the whole duration of each track segment. TWS represents how much a track segment is confined to a twisted ribbon. The value of TWS is reported in logarithm to the base 10. For example, a track segment with 10 radians of accumulated osculating plane angle change and 1 radians of mean linear-fit error would have a TWS of 1.

Digital Classification of Sperm Trajectories

The 3D swimming patterns of sperms were classified based on the dynamic parameters defined above. Note that all the horse sperm trajectories with VCL smaller than 60 μm/sec and VSL smaller than 20 μm/sec are considered as immotile and are excluded from the reported statistics. The following are the specific criteria used in this work to distinguish different categories of horse sperm trajectories:

Ribbon trajectory: TWS≥1.2.

Hyperactivated trajectory: VCL≥180 μm/sec and ALH≥12 μm.

Hyper-ribbon trajectory: A hyper-activated trajectory that also forms a ribbon (TWS≥1.2).

Because human sperm trajectories were recorded at a lower frame rate (92 FPS instead of 143 FPS), the criteria for categorizing these trajectories for human sperms were modified as such:

Immotile trajectory: VCL<30 nm/sec.

Ribbon trajectory: TWS≥1.3.

Hyperactivated trajectory: VCL≥150 nm/sec; LIN≤0.5 and ALH≥7 μm

The other criteria remained the same as the ones used for horse sperms.

Automated processing of 3D sperm trajectory data

Data processing procedures, including the reconstruction of lens-free holographic images, the localization of sperms' 3D centroids, the resolution of sperms' connected 3D spatio-temporal trajectories from each other, and the classification of their 3D swimming patterns were all performed with an automated program running on Matlab. The typical computation time for automatic processing of e.g., ~5,000 lens-free images from a single semen sample is ~4 hours (using Matlab R2011a running on a PC with an eight-core Intel Core i7-930 2.80 GHz processor).

Results

Using the dual-view and dual-wavelength holographic on-chip microscopy platform, reconstructed 3D spatio-temporal trajectories images were obtained of horse sperms within large sample volumes (~9 μL) at ~140 FPS. Based on these experiments, horse sperms were observed to display a unique 'chiral ribbon' pattern. The chiral ribbon pattern is seen in FIGS. 9A-9F and 10A-10D, which occurs with a frequency of ~27.3% among 9,625 individual 3D trajectories that were reconstructed using the high-throughput on-chip imaging platform. These horse sperms that follow a chiral ribbon swimming pattern have locally planar lateral displacements as if they are confined in 2D. In contrast to regular planar trajectories, however, in a chiral ribbon the plane on which the lateral displacements occur rotates continuously around a central axis as the sperm is moving forward, forming a 'twisted' ribbon within e.g., a ~0.7-sec long segment of the sperm trajectory (see FIG. 9B and FIG. 9E). Not only that this twisted ribbon trajectory is quite tight with a typical side-to-side displacement of ~5 μm, but also it beats rather fast, crossing over the central axis roughly 30 times within a second, making it rather challenging to observe with other 3D optical tracking techniques due to the tight requirements in 3D localization accuracy and video frame rate.

Further investigation of these chiral ribbon swimming patterns in horse sperm samples revealed that in longer durations of observation (>2.1 sec), one can also observe spatio-temporal super-structures that mimic a different type of a chiral ribbon, namely a "helical ribbon" (see e.g., FIGS. 9A and 9D. With this type of super-structure, the osculating plane of the sperm trajectory (i.e., the beating of the sperm head) not only twists as the sperm moves forward, but also forms a 3D helix in the form of a chiral ribbon. It should be emphasized that such a helical ribbon trajectory should not be confused with already-known helical trajectories of sperms, where the sperm head defines a simple helix, not a 3D ribbon (i.e., without any chiral planar motion). As a matter of fact, the chiral ribbon swimming patterns cannot be represented by already known patterns of sperms or other micro-swimmers and is enabled by the high-throughput on-chip imaging platform. The same lens-free imaging system also permits one to track each one of these ~1,000 horse sperms (per experiment) within a large sample volume of ~9 μL across a time window of e.g., ~7-10 sec (at ~140 FPS), and analyze the spatio-temporal transitions of their swimming patterns into or out of the chiral ribbon pattern. FIGS. 10A-10D illustrate such a swimming pattern transition observed when an individual horse sperm encountered the bottom glass surface of the sample holder, where its 3D trajectory switched from a right-handed chiral ribbon pattern to a simple planar swimming pattern. This example illustrates that boundary confinement could be an influential factor in the transitions of sperm swimming patterns.

The 3D motion dynamics was also statistically quantified including the Rate of Twisting (RTW), Linearity (LIN), Straight-Line Velocity (VSL), Curvilinear Velocity (VCL), and Amplitude of Lateral Head Displacement (ALH) of the chiral ribbon trajectories observed in horse sperms. For this statistical analysis, 2,625 individual chiral ribbon patterns were digitally processed (out of a total of 9,625 trajectories, each ~0.7 sec long). FIG. 11A illustrates a graph of VCL vs. VSL for 2625 ribbon tracks. FIG. 11B illustrates LIN vs. ALH for 2625 ribbon tracks. As seen in FIG. 11C, ~85% of the ribbon horse sperm trajectories prefer left-handed twisting over right-handed twisting, exhibiting a side-to-side displacement of 1-12 μm and a twisting rate (RTW) of 0.5-22 rad/sec.

After discovering chiral ribbon trajectories in horse sperm samples, additional searches were performed for similar 3D swimming patterns in human sperms. To this end, 24,090 individual human sperm trajectories were processed to find out that only ~1.7% of the time chiral ribbons were formed. This lower percentage also partially explains why this twisted ribbon type of swimming pattern remained unidentified in earlier studies and was in fact broadly classified as part of the "typical" trajectories for human sperms. Despite their low percentages, it was still observed that right-handed twisting in human sperm ribbons is more frequent than left-handed twisting (1.1% vs. 0.6% of 24,090 trajectories), which is quite the opposite of what is observed with horse sperm ribbons. Another interesting difference between the chiral ribbons of these two species is that human sperms, even in longer observation time windows, still follow twisted ribbons rather than helical ribbons.

DISCUSSION

Mathematically, the equation of a 'chiral ribbon' surface s can be broadly defined as:

$$s = \begin{bmatrix} x \\ y \\ z \end{bmatrix} = \begin{bmatrix} r_h \cos\left(2\pi \frac{l}{p_h} + \theta_h\right) \\ r_h \sin\left(2\pi \frac{l}{p_h} + \theta_h\right) \\ l \end{bmatrix} + \frac{a}{\sqrt{1 + \left(2\pi \frac{r_h}{p_h}\right)^2}} \begin{bmatrix} \sin\left(2\pi \frac{l}{p_h} + \theta_h\right) \\ -\cos\left(2\pi \frac{l}{p_h} + \theta_h\right) \\ 2\pi \frac{r_h}{p_h} \end{bmatrix} \quad (1)$$

where $0 \leq l \leq L$, $$\frac{-D}{2} \leq a \leq \frac{D}{2},$$

L is the length of the chiral ribbon that is aligned along the z-direction, D and $r_h$ are the width and the radius of the chiral ribbon, respectively, $p_h$ is the pitch of the chiral ribbon (defined as positive for a right-handed ribbon and negative for a left-handed ribbon), and $\theta_h$ is the offset angle of the chiral ribbon. This chiral ribbon equation can form a "helical" or a "twisted" ribbon when $r_h$ is significantly larger than zero or close to zero, respectively.

The chiral ribbons observed in the sperm tracking experiments can be mathematically reproduced by adding a periodic lateral oscillation (e.g., sinusoidal) along the ribbon surface that is defined by equation 1, i.e., $$\begin{bmatrix} x \\ y \\ z \end{bmatrix} = \begin{bmatrix} r_h \cos(\omega_h t + \theta_h) \\ r_h \sin(\omega_h t + \theta_h) \\ v_z t \end{bmatrix} + \frac{r_b \cos(\omega_b t + \theta_b)}{\sqrt{v_z^2 + \omega_h^2 r_h^2}} \begin{bmatrix} v_z \sin(\omega_h t + \theta_h) \\ -v_z \cos(\omega_h t + \theta_h) \\ \omega_h r_h \end{bmatrix}, \quad (2)$$

where $v_z$ is the forward-moving velocity along the z direction, $\omega_h = 2\pi(v_z/p_h)$ is the angular velocity of the helical ribbon (positive for a right-handed ribbon and negative for a left-handed one), $r_b$ is the radius of the sperm beating waveform, $\omega_b$ and $\theta_b$ are the angular velocity and the offset angle of the same beating waveform. Two examples of simulated sperm trajectories that are computed based on equation 2 are shown in FIGS. 9C and 9F, with their parameters (Table 3 below) tuned to match the measured chiral ribbon trajectories of FIGS. 9A and 9D, respectively. Note that the osculating planes of the measured sperm trajectories reported in FIGS. 9A and 9D are in very good agreement with the theoretical trajectories shown in FIGS. 9C and 9F, respectively, both calculated based on equation 2 with the parameters of Table 4 below.

TABLE 4

| | $r_h$ (μm) | $\omega_h$ (rad/sec) | $\theta_h$ (rad) | $r_b$ (μm) | $\omega_b$ (rad/sec) | $\theta_b$ (rad) | $v_z$ (μm/sec) |
|---|---|---|---|---|---|---|---|
| FIG. 9C | 3.0 | −4.7 | −0.3 | 2.0 | 188.5 | 0.5 | 40.0 |
| FIG. 9F | 10.0 | −5.7 | 3.5 | 3.0 | 125.7 | 0.0 | 20.0 |

Interestingly, when $r_h=0$, the "twisted" ribbon surface exactly becomes a minimal surface in the form of a helicoid (which should not be confused with a helix). Minimal surfaces minimize their surface area with respect to a particular boundary, and also have local mean curvature equal to zero at all points on their surface. Besides a helicoid, a simple plane and a catenoid also define minimal surfaces. The mean curvature (H) of a chiral ribbon surface can be computed from the partial derivatives of s with respect to its parameters, 1 and can be written as:

$$H = \frac{(s_l \cdot s_l)(s_{aa} \cdot \hat{n}) - 2(s_l \cdot s_a)(s_{la} \cdot \hat{n}) + (s_a \cdot s_a)(s_{ll} \cdot \hat{n})}{2((s_l \cdot s_l)(s_a \cdot s_a) - (s_l \cdot s_a)^2)} \quad (3)$$

where subscripts indicate partial derivatives (e.g., $s_l = \partial s/\partial l$), and $\hat{n} = (s_l \times s_a)/\|s_l \times s_a\|$ is the unit normal vector. For the chiral ribbon surfaces defined by equation 1, the mean curvature can be calculated as:

$$H = \frac{-r_h}{2\sqrt{\left(\frac{p_h}{2\pi}\right)^4 + r_h^4 + \left(\frac{p_h}{2\pi}\right)^2(2r_h^2 + a^2)}} \quad (4)$$

As the term inside the square root is strictly positive in equation 4, H=0 and s is a minimal surface if and only if $r_h$=0, proving that an ideal twisted ribbon indeed defines a minimal surface.

It should be emphasized that the actual cause and the biological function of these chiral ribbon swimming patterns are not clear. In many of the situations where minimal surfaces arise, a common theme is that of energy minimization. Hence, the fact that different modes of sperm locomotion (e.g., twisted ribbon as well as simple planar trajectories) follow a minimal surface may also indicate energy minimization corresponding to maximal propulsion efficiency in these modes. Another related speculative cause is that a small asymmetry in the shape or the location of the center-of-mass of the sperm head might generate a net torque through the surrounding fluid when the sperm tail is pushing its body forward. Similar phenomena have been discussed previously using hydrodynamics numerical simulations to partially explain regular helical trajectories (not chiral ribbons) of sperm cells. Based on such a structural asymmetry, the local movement of the sperm head can still be governed by the planar beating of its tail, however the whole body can gradually rotate due to a net torque and the sperm trajectory can slowly deviate from the central axis of the beating. Once the whole sperm body finishes a full rotation, the trajectory would also complete a cycle of the helical ribbon. As for the biological function of such a chiral ribbon swimming pattern, it might possibly be similar to what has been proposed for regular helical trajectories; in other words, these chiral swimming patterns could potentially help reorienting the motion of the micro-organisms into the direction of stimulus gradient due to for example the concentration of a chemo-attractant or just the environmental temperature distribution. These chiral ribbons that were observed, compared to simple planar trajectories, might permit sperms to sense such gradient profiles over larger 3D volumes, which could then help detection of weaker stimuli, assisting in e.g., sperms' chemotaxis or thermotaxis behavior.

Experimental Data #3-3D Tracking of Equine Sperm

Using the high-throughput optical tracking technique that is based on partially-coherent digital in-line holography, a detailed analysis of the statistical behavior of horse sperms' three-dimensional (3D) swimming dynamics was conducted. This dual-color and dual-angle lens-free imaging platform enables one to track individual 3D trajectories of ~1,000 horse sperms at sub-micron level within a sample volume of ~9 µL at a frame rate of 143 frames per sec (FPS) and collect thousands of sperm trajectories within a few hours for statistical analysis of their 3D dynamics. Over 17,000 horse sperm trajectories were recorded that can be grouped into six major categories: irregular, linear, planar, helical, ribbon, and hyperactivated, where the hyperactivated swimming patterns can be further divided into four sub-categories, namely hyper-progressive, hyper-planar, hyper-ribbon, and star-spin. The large spatio-temporal statistics that were collected with this 3D tracking platform revealed that irregular, planar, and ribbon trajectories are the dominant 3D swimming patterns observed in horse sperms, which altogether account for >97% of the trajectories that were imaged in plasma-free semen extender medium. It was also discovered that horse seminal plasma in general increases sperms' straightness in their 3D trajectories, enhancing the relative percentage of linear swimming patterns and suppressing planar swimming patterns, while barely affecting the overall percentage of ribbon patterns.

Preparation of Horse Sperm Suspension

Frozen sperm specimens of a Warmblood stallion were obtained from the Center for Equine Health at the University of California, Davis (under UC Davis IACUC protocol #15770). Before freezing, equine semen extender (E-Z Mixin BFT, Animal Reproduction Systems) was used to dilute fresh semen specimens to a concentration of 50 million sperms per ml. After centrifugation at 400G for 15 min, the pellet was re-suspended in freezing extender (E-Z Freezin Equine Semen Extender, Animal Reproduction Systems) with a final concentration of 400 million sperms per ml. The processed sperm specimens were then frozen in a programmable freezer. The straws (each 0.5 mL) were plunged into liquid nitrogen for storage once they reached –150° C.

To prepare the horse sperm suspension for imaging, the frozen specimens were thawed in water bath (38° C.) for 0.5 min, and then rehydrated for 15 min by mixing (a ratio of 1:1) with equine semen extender (BotuSemen, Nidacon, Sweden). After rehydration, the semen specimens were centrifuged with isotonic density medium (Equipure, Nidacon, Sweden) at 200 G for 30 min to increase the specimen motility to >50% and then incubated for another 30 min. Disposable sample holders were prepared by taping a laser-cut Acetal film (~0.15 mm thick) between two pieces of No. 1 cover slips to hold the sperm suspension (~25 µL) during lens-free computational imaging experiments.

Culture media with four different horse seminal plasma concentrations were used in this work to observe seminal plasma's effect on the 3D swimming patterns of horse sperms: (i) Baseline medium: the original equine semen extender without any seminal plasma; (ii) Modified medium I: equine semen extender with 10% (v %) seminal plasma added; (iii) Modified medium II: equine semen extender with 20% (v %) seminal plasma added; (iv) Modified medium III: equine semen extender with 30% (v %) seminal plasma added.

Dual-View and Dual-Color Lens-Free on-Chip Tracking Set-Up

A dual-view and dual-color lens-free computational imaging setup was used similar to those described herein (e.g., FIG. 1A). In this setup, two partially-coherent light sources (LED-coupled multimode fibers, each with a core size of 0.4 mm) illuminated the sample holder from two different angles using two different wavelengths (vertical one: red, 625 nm; oblique one at 45°: blue, 470 nm). The sample holder containing the sperm samples was placed directly on the top of the protection glass of a monochrome image sensor-array (Aptina MT9P031STC, 5 megapixels, 2.2 nm pixel size) to record the 3D movement of horse sperms, where the temperature was kept at 37-39° C. by cutting off the power of the image sensor between video acquisition periods.

The faster movement of horse sperms compared to human sperms, with a beat-cross frequency (BCF) of ~30 Hz and an instantaneous speed of ~0.15 mm/sec, required an increase in the frame rate of the imaging system to 143 frames per sec (FPS) and a decrease in the exposure time to ~3.0 ms for oversampling the 3D horse sperm movement without motion-blur. Accordingly, the whole field-of-view (FOV) of the image sensor was digitally divided into 50 smaller regions-of-interest (ROIs), which were sequentially recorded for continuous intervals of 0.7-7.0 seconds each. Digitally scanning over 50 such ROIs (with >5,000 lens-free holographic frames) and recording the trajectories of >1,000 horse sperms took ~30 min for each semen sample.

Reconstruction of 3D Horse Sperm Trajectories

Every 100 consecutive lens-free frames in the video sequence of the same ROI were first averaged to generate a stationary lens-free image. Each lens-free holographic image was then subtracted from its nearest stationary averaged image to digitally remove the lens-free static holograms of non-moving objects within the ROI, which could be either due to dead sperms within the specimen or due to un-dissolved solute from semen extender powder. The holographic reconstruction procedures as described herein were then used to recover the 3D trajectories of mobile sperms inside the FOV of the image sensor. Briefly, on all the possible planes, the vertical and oblique projections of each sperm head were digitally reconstructed and their centroid positions were calculated in these reconstructed lens-free amplitude images. The centroid position of the vertical projection directly provides the x and y coordinates of the sperm, while its z coordinate can be determined by the distance between its vertical and oblique projection. Repeating the same 3D localization procedures on all holographic frames would then generate a space-time matrix containing the spatial and temporal coordinates of all the sperms within the observation volume. Finally, a Brownian-statistics-based algorithm was used to link the detected points across the recorded lens-free frames and reconstruct the entire 3D trajectory of each horse sperm over a time window of e.g., 0.7-7 seconds.

Dynamic Parameters of 3D Swimming Patterns

A series of digital parameters, such as straight-line velocity, curvilinear velocity, etc. were extracted from individual reconstructed sperm trajectories to quantify the 3D swimming dynamics of horse sperms. Either 0.7 sec-long trajectories (~100 frames at 143 FPS) or digitally cropped track segments of similar length were used for extracting these parameters. Before this parameter extraction process, the horse sperm trajectories were digitally "straightened" to simplify the analysis of sperm lateral displacements. The definitions of straight-line velocity (VSL), curvilinear velocity (VCL), linearity, amplitude of lateral head displacement (ALH), beat-cross frequency (BCF), rotation speed (RPS), and number of stable turns (NST) are the same as discussed herein previously. Newly introduced 3D swimming parameters are defined as follows:

Planarity (PLN) is defined as the correlation coefficient between the lateral coordinates, $X_r$ and $Y_r$, of all the position points in a "straightened" track segment. PLN represents how much a sperm's beating pattern is confined to an unbent plane.

Rate of twisting (RTW) represents the rotation speed of the head beating plane for a sperm swimming in a ribbon pattern and it is defined as the angular frequency of the linear function that best fits the time evolution of the osculating plane angle for a track segment (unit: rad/sec). The osculating plane angle on each position point along the track segment is determined by finding the lateral displacements' mean azimuthal angle in a beating cycle, whose duration is defined by 2/BCF.

Twisting stability (TWS) represents how much a track segment is confined to a twisted ribbon. It is defined as the ratio between the accumulated angle rotation of the osculating plane and the averaged error to the best-fit linear function in the osculating plane angle. Both the accumulated angle rotation and the root-mean-square averaged fitting error were calculated across the whole duration of each track segment. The value of TWS is reported in log-scale; for example, a track segment with 10 radians of accumulated osculating plane rotation and 0.1 radian of mean linear-fit error would have a TWS of 2.

Digital Classification of Horse Sperm Trajectories

The dynamic parameters defined in the previous subsection were the basis of 3D swimming pattern classification of horse sperms. All the sperm trajectories with a VSL smaller than 20 μm/sec and a VCL smaller than 60 μm/sec were treated as immotile and were not counted into the reported statistics. The following specific criteria were used in this work to identify individual patterns of 'motile' horse sperm trajectories:

Linear trajectory: LIN≥0.7.
Planar trajectory: PLN≥0.8.
Helical trajectory: NST≥2.0.
Ribbon trajectory: TWS≥1.2.
Hyperactivated trajectory: VCL≥180 μm/sec and ALH≥12 μm.
Hyper-planar trajectory: a hyperactivated trajectory that is also planar.
Hyper-helical trajectory: a hyperactivated trajectory that is also helical.
Hyper-ribbon trajectory: a hyperactivated trajectory that is also ribbon.
Star-spin (hyper-nonprogressive) trajectory: a hyperactivated trajectory with a VSL<30 μm/sec.
Hyper-progressive trajectory: a hyperactivated trajectory that is not planar, helical, or ribbon.
Irregular trajectory: a motile trajectory that does not fit into any of the above categories.

Digital Processing of 3D Sperm Trajectory Data

Including the digital reconstruction of lens-free holographic images, localization of sperms' 3D centroids, spatio-temporal linking of sperms' trajectory points, and categorization of 3D swimming patterns were all performed with a fully-automated custom-designed Matlab program. The typical computation time for automatic processing of e.g., ~5,000 lens-free holographic images from a single horse semen sample is ~4 hours in Matlab R2011a running on a PC with an Intel Core i7-930 2.80 GHz processor.

Results and Discussion

Figure 1C:
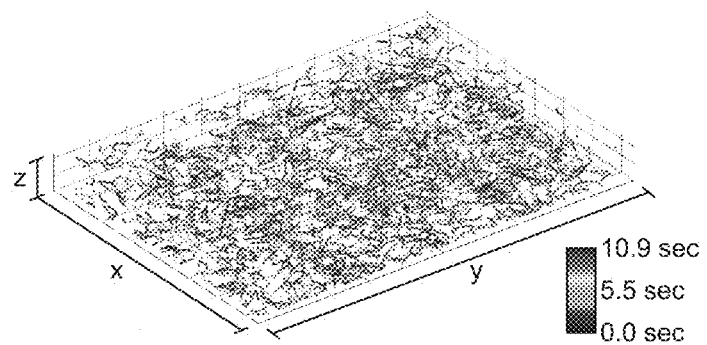
FIG. 1C illustrates the reconstructed 3D spatio-temporal trajectories of sperm in a three dimensional volume.

The throughput of the dual-view and dual-color lens-free on-chip imaging system enables one to track the individual 3D trajectories of ~1,000 horse sperms in a sample volume of ~9 μL across a time window of for example ~7.0 sec as seen in the 3D spatio-temporal view of FIG. 1C. This large sample volume enables the collection of thousands of sperm trajectories at a frame rate of 143 FPS within a few hours of on-chip imaging experiments. Using this computational imaging approach, >17,000 horse sperm trajectories were recorded, which display a variety of 3D swimming patterns that can be grouped into six major categories, namely, irregular, linear, planar, helical, ribbon, and hyperactivated. FIG. 12A illustrates an irregular trajectory. FIG. 12B illustrates a linear trajectory. FIG. 12C illustrates a planar trajectory. FIG. 12D illustrates a helical trajectory. FIG. 12E illustrates a ribbon trajectory. FIG. 12F illustrates a hyper-activated (hyper-progressive) trajectory. The "irregular" trajectory shown in FIG. 12A represents the 3D trajectories that do not display a distinct swimming pattern (unlike e.g., linear, planar, helical, ribbon or hyperactivated patterns) and it accounts for ~35% of the observed horse sperm trajectories as seen in Table 5 below. In this category, the horse sperm moves forward along a slightly curved axis with an irregular lateral displacement that is approximately 4 μm side-to-side.

displacement are greatly increased (VCL≥180 μm/sec; ALH≥12 μm). Just like the irregular and planar trajectories that can become hyper-progressive and hyper-planar after

TABLE 5

| Irregular | Planar | Ribbon | Linear | Helical | Hyper-progressive | Hyper-planar | Hyper-ribbon | Star-spin |
|---|---|---|---|---|---|---|---|---|
| 34.8% (±7.8%) | 36.7% (±7.4%) | 26.3% (±7.6%) | 0.1% (±0.2%) | 0.1% (±0.2%) | 0.4% (±0.7%) | 0.6% (±0.5%) | 0.9% (±0.9%) | 0.0% (±0.0%) |

Table 4 shows the relative percentages of different swimming patterns for horse sperms. These patterns were observed in 27 measurements of 4 semen specimens, containing 9,625 motile horse sperms. The standard deviations listed in parentheses were obtained by calculating the deviation of each ratio observed across all the 27 measurements. These measurements were all made in plasma-free baseline medium (BotuSemen) after >30 min of incubation. The statistics of planar and ribbon patterns also include hyper-planar and hyper-ribbon trajectories, respectively.

In other categories of trajectories, horse sperms display repeatable and distinct swimming patterns that can be automatically detected and characterized. For example, sperms with linear trajectory (see e.g., FIG. 12B) move forward very swiftly (typically at a VSL of >80 μm/sec) with relatively small lateral displacements (typically ~1-3 μm side-to-side). Therefore, the whole trajectory looks like a straight line in 3D space. In another category, sperms with planar trajectories (see e.g., FIG. 12C) display periodic lateral displacements that are mostly confined to a two-dimensional plane. This swimming pattern is typically observed near the boundaries of the sample holder and it accounts for ~37% of the horse sperm trajectories that were reconstructed (see Table 4). Helical trajectories with stable rotations, as exemplified in FIG. 12D, are very rare for horse sperms (~0.1%, see Table 4) and their revolutions are typically distorted.

An interesting swimming pattern that was observed in horse sperms is the one that forms ribbons (see e.g., FIG. 12E). Based on the 3D trajectories reconstructed by the lens-free computational imaging system, horse sperms with this swimming pattern have locally planar lateral displacements, where the plane continuously rotates around a central axis as the horse sperm is moving forward, forming a twisted ribbon within a 0.7-sec long segment of the sperm trajectory. ~27% of horse sperm trajectories belong to this category, i.e., the ribbon pattern (see Table 4).

In the final major category of horse sperm swimming patterns, hyperactivated trajectories were observed (see FIG. 12F), in which both the instantaneous speed and the lateral hyperactivation, ribbon trajectories can also turn hyperactivated with an enlarged lateral displacement and a fastened osculating plane rotation. In the baseline medium, hyperactivated swimming patterns are only displayed by a relatively small portion of the whole sperm population. All these sub-categories of hyperactivated swimming patterns (hyper-progressive, hyper-planar, hyper-ribbon, and star-spin) together constitute ~1.9% of horse sperm trajectories (see Table 4).

The large pool of 3D trajectory data that was collected using the lens-free computational imaging platform also permits one to statistically quantify the dynamics of horse sperm swimming patterns. For example, the statistical behavior of 9,625 horse sperms in baseline medium with various swimming patterns are quantified through a series of parameters, such as straight-line velocity (VSL), curvilinear velocity (VCL), linearity (LIN), amplitude of lateral head displacement (ALH), beat-cross frequency (BCF) and are compared to the swimming dynamics of only the horse sperms with ribbon trajectories. An interesting observation is that ~85% of the ribbon horse sperm trajectories prefer left-handed twisting over right-handed twisting, exhibiting a twisting rate of 0.5-22 rad/sec and a side-to-side displacement of 1-12 μm.

The lens-free on-chip imaging system's large imaging volume and wide temporal observation window also enable one to register and characterize horse sperms' transitions in and out of individual swimming patterns. Based on 596 extended 3D trajectories (each more than 2.1 sec long) that are reconstructed by the lens-free imaging system, Table 6 summarizes the frequency of these transitions observed among different swimming patterns of horse sperms. These results reveal that horse sperms do not switch their swimming patterns very often (i.e., only 144 pattern transitions were observed within an accumulated track duration of 1,840-sec; stated differently less than one transition occurs every 12 sec on average). Furthermore, most of these transitions (~73% of 144 pattern transitions that were observed) happen between the three most prevalent categories, namely irregular, planar, and ribbon patterns.

TABLE 6

| | To | | | | | | | | | |
|---|---|---|---|---|---|---|---|---|---|---|
| From | Irregular | Planar | Ribbon | Helical | Linear | Hyper-progressive | Hyper-planar | Hyper-ribbon | Hyper-helical | Star-spin |
| Irregular (256.6 sec) | | 16 | 5 | 0 | 0 | 2 | 0 | 0 | 0 | 1 |
| Planar (888.7 sec) | 35 | | 18 | 0 | 0 | 3 | 1 | 0 | 0 | 0 |
| Ribbon (597.9 sec) | 8 | 36 | | 0 | 0 | 3 | 0 | 2 | 0 | 0 |
| Helical (14.9 sec) | 1 | 2 | 1 | | 0 | 0 | 0 | 0 | 0 | 0 |

TABLE 6-continued

| From | Irregular | Planar | Ribbon | Helical | Linear | Hyper-progressive | Hyper-planar | Hyper-ribbon | Hyper-helical | Star-spin |
|---|---|---|---|---|---|---|---|---|---|---|
| Linear (1.5 sec) | 0 | 1 | 0 | 0 |  | 0 | 0 | 0 | 0 | 0 |
| Hyper-progressive (15.4 sec) | 3 | 0 | 0 | 0 | 0 |  | 1 | 0 | 0 | 0 |
| Hyper-planar (19.5 sec) | 0 | 0 | 0 | 0 | 0 | 1 |  | 0 | 0 | 0 |
| Hyper-ribbon (38.8 sec) | 1 | 2 | 0 | 0 | 0 | 0 | 0 |  | 0 | 0 |
| Hyper-helical (0.0 sec) | 0 | 0 | 0 | 0 | 0 | 0 | 0 | 0 |  | 0 |
| Star-spin (4.9 sec) | 1 | 0 | 0 | 0 | 0 | 0 | 0 | 0 | 0 |  |

To better understand the properties of the swimming patterns for horse sperms, the sperms' statistical behavior was attempted to be modified by adding horse seminal plasma back to the sperm culture media. In terms of the percentages of individual swimming patterns, linear and planar patterns were clearly affected by the presence of the horse seminal plasma, enhancing the linear patterns while suppressing the planar patterns, but the percentage of ribbon sperm trajectories did not show a statistically significant change in the modified culture media containing horse seminal plasma as seen in FIG. 1. The effect of seminal plasma on sperm movement can also be quantified through the sperm trajectories' dynamical parameters. In general, horse seminal plasma enhances sperms' straightness in their 3D trajectories and slows down their beating. A similar enhancement in straightness of sperm swimming patterns was also observed among ribbon trajectories resulting in faster twisting. On the other hand, a linear relationship between these dynamical parameters and the plasma concentration was not observed in these experiments.

While embodiments have been shown and described, various modifications may be made without departing from the scope of the inventive concepts disclosed herein. The invention(s), therefore, should not be limited, except to the following claims, and their equivalents.

What is claimed is:

1. A system for three dimensional imaging of motile objects contained within a sample comprising: an image sensor; a sample holder configured to hold the sample, the sample holder disposed adjacent to the image sensor; a first illumination source having a first wavelength and positioned relative to the sample holder at a first location to illuminate the sample; a second illumination source having a second wavelength, different from the first wavelength, and positioned relative to the sample holder at a second location, different from the first location, to illuminate the sample, and wherein both the first illumination source and the second illumination source illuminate the sample from the same side of the sample holder; at least one digital processor configured to receive a plurality of image frames generated by the image sensor; and wherein the first illumination source and the second illumination source are configured to simultaneously illuminate the sample contained within the sample holder over a period of time and wherein the at least one digital processor receives the plurality of image frames and identifies holographic projections and microscopic images of the motile objects from the first illumination source and the second illumination source and reconstructs a three dimensional trajectory of the motile objects observed over the period of time based on the acquired holographic projections and classifies the three dimensional trajectory of the motile objects into one or more types of trajectories.

2. The system of claim 1, wherein the motile objects comprise sperms.

3. The system of claim 1, wherein the first illumination source and the second illumination source comprise, respectively, a first LED and a second LED.

4. The system of claim 3, wherein the first and second LEDs are, respectively, butt-coupled to optical fibers.

5. The system of claim 1, further comprising a programmable power relay configured to cycle the image sensor between an ON state and an OFF state to maintain the sample holder at a regulated temperature between 36-37° C.

6. The system of claim 1, further comprising a heat sink in thermal contact with the image sensor.

7. The system of claim 1, wherein the first location of the first illumination source is angled relative to the second location of the second illumination source.

8. The system of claim 7, wherein the angle between the first location and the second location is within the range of 20° to 60°.

9. The system of claim 1, wherein the sample holder has a depth of field within the range of 0.01 mm to 5.0 mm.

10. The system of claim 1, wherein the at least one digital processor comprises a computer processor.

11. The system of claim 1, wherein the at least one digital processor further reconstructs microscopic images of the stationary objects.

12. A method for three dimensional tracking of motile objects contained within a sample comprising: simultaneously illuminating a sample holder containing the motile objects with a first illumination source and a second illumination source wherein the first illumination source and the second illumination source are located at different positions from one another and emit light at the same or different wavelengths, and wherein both the first illumination source and the second illumination source illuminate the motile objects from the same side of the sample holder; obtaining a plurality of image frames over time of the motile objects with an image sensor disposed adjacent to the sample holder while the sample holder is illuminated; digitally reconstructing a projection image of the motile objects in each frame based on illumination originating from the first illumination source; digitally reconstructing a projection image of the motile objects in each frame based on illumination originating from the second illumination source; identifying the x, y, and z positions of the motile objects in each frame based on the digitally reconstructed projection images of the motile objects obtained from the first and second illumination sources; connecting the x, y, and z positions of the motile objects over a plurality of frames to form a three-dimensional track of the motile objects within the sample; and automatically classifying, by at least one processor, the three-dimensional tracks of the sperm into one of a plurality of categories.

13. The method of claim 12, wherein the motile objects comprise sperm.

14. The method of claim 13, wherein the sperm comprises human sperm or equine sperm.

15. The method of claim 12, wherein the categories comprise: typical, helical, ribbon, hyper-ribbon, hyper-activated, and hyper-helical.

16. The method of claim 15, wherein the ribbon category comprises one of a chiral ribbon, helical ribbon, or twisted ribbon.

17. The method of claim 12, wherein each image frame was divided into a plurality of regions-of-interest.

18. A method for three dimensional tracking of motile objects contained within a sample comprising: sequentially illuminating a sample holder containing the motile objects with a first illumination source and a second illumination source wherein the first illumination source and the second illumination source are located at different positions from one another and emit light at the same or different wavelengths, and wherein both the first illumination source and the second illumination source illuminate the motile objects from the same side of the sample holder; obtaining a plurality of image frames over time of the motile objects with an image sensor disposed adjacent to the sample holder while the sample holder is illuminated; digitally reconstructing a projection image of the motile objects in each frame based on illumination originating from the first illumination source; digitally reconstructing a projection image of the motile objects in each frame based on illumination originating from the second illumination source; identifying the x, y, and z positions of the motile objects in each frame based on the digitally reconstructed projection images of the motile objects obtained from the first and second illumination sources; connecting the x, y, and z positions of the motile objects over a plurality of frames to form a three-dimensional track of the motile objects within the sample; and automatically classifying, by at least one processor, the three-dimensional tracks of the sperm into one of a plurality of categories.

19. The method of claim 18, wherein the motile objects comprise sperm.

20. The method of claim 19, wherein the sperm comprises human sperm.

21. The method of claim 19, wherein the sperm comprises equine sperm.

22. The method of claim 18, wherein the categories comprise: typical, helical, ribbon, hyper-ribbon, hyper-activated, and hyper-helical.

23. The method of claim 22, wherein the ribbon category comprises one of a chiral ribbon, helical ribbon, or twisted ribbon.

24. The method of claim 18, wherein each image frame was divided into a plurality of regions-of-interest.

* * * * *